I

(12) United States Patent
Hinek et al.

(10) Patent No.: US 9,283,236 B2
(45) Date of Patent: *Mar. 15, 2016

(54) ALDOSTERONE INDUCED VASCULAR ELASTIN PRODUCTION

(71) Applicants: HUMAN MATRIX SCIENCES, LLC, Visalia, CA (US); THE HOSPITAL FOR SICK CHILDREN, Toronto (CA)

(72) Inventors: Aleksander Hinek, Toronto (CA); Thomas F. Mitts, Visalia, CA (US)

(73) Assignees: The Hospital for Sick Children, Toronto, ON (CA); Human Matrix Sciences, LLC, Visalia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/058,181

(22) Filed: Oct. 18, 2013

(65) Prior Publication Data

US 2014/0056916 A1    Feb. 27, 2014

Related U.S. Application Data

(63) Continuation of application No. 12/937,534, filed as application No. PCT/US2009/046582 on Jun. 8, 2009, now Pat. No. 8,618,084.

(60) Provisional application No. 61/059,475, filed on Jun. 6, 2008, provisional application No. 61/059,288, filed on Jun. 6, 2008.

(51) Int. Cl.
| | | |
|---|---|---|
| *A61K 31/58* | (2006.01) | |
| *A61P 9/10* | (2006.01) | |
| *A61K 31/585* | (2006.01) | |
| *A61K 31/573* | (2006.01) | |
| *A61K 45/06* | (2006.01) | |
| *C07J 17/00* | (2006.01) | |
| *C07J 21/00* | (2006.01) | |
| *C07K 14/78* | (2006.01) | |

(52) U.S. Cl.
CPC .............. *A61K 31/585* (2013.01); *A61K 31/573* (2013.01); *A61K 31/58* (2013.01); *A61K 45/06* (2013.01); *C07J 17/00* (2013.01); *C07J 21/00* (2013.01); *C07K 14/78* (2013.01)

(58) Field of Classification Search
None
See application file for complete search history.

(56) References Cited

U.S. PATENT DOCUMENTS

| | | | |
|---|---|---|---|
| 4,543,351 A | 9/1985 | Messina | |
| 5,700,794 A | 12/1997 | Clark | |
| 5,885,974 A | 3/1999 | Danielov | |
| 6,303,588 B1 | 10/2001 | Danielov | |
| 8,148,327 B2 | 4/2012 | Mitts et al. | |
| 8,470,774 B2 | 6/2013 | Hinek et al. | |
| 8,618,084 B2 | 12/2013 | Hinek et al. | |
| 2007/0275938 A1 | 11/2007 | Reading et al. | |
| 2012/0195914 A1 | 8/2012 | Mitts et al. | |

FOREIGN PATENT DOCUMENTS

| | | |
|---|---|---|
| DE | 2401446 A1 | 7/1974 |
| FR | 2213776 A1 | 9/1974 |
| JP | 60028927 A | 2/1985 |
| WO | WO 96/17621 A | 6/1996 |
| WO | WO 97/42970 A1 | 11/1997 |
| WO | WO 2008/154389 A1 | 12/2008 |

OTHER PUBLICATIONS

Banker et al. "Modern Pharmaceutics" 1979, *Marcel Dekker, Inc., New York* (TOC).
Bunda et al. "Aldosterone Induces Elastin Production in Cardiac Fibroblasts through Activation of Insulin-Like Growth Factor-I Receptors in a Mineralocorticoid Receptor-Independent Manner" 2007, *Am. J. Path.* 171:809-819.
Bunda et al. "Aldosterone Stimulates Elastogenesis in Cardiac Fibroblasts Via Mineralocorticoid Receptor-Independent Action Involving the Consecutive Activation of Gα13, c-Src, the Insulin-Like Growth Factor-I Receptor, and Phosphatidylinositol 3-Kinase/Akt" Jun. 12, 2009, *Journal of Biological Chemistry* 284(24):16633-16647.
Bunda "Aldosterone and its Antagonists Modulate Elastin Deposition in the Heart" 2008, Graduate Thesis, 210 pages as printed.
Chai et al. "Genomic and nongenomic effects of aldosterone in the rat heart: why is spironolactone cardioprotective?" 2005, *Br. J. of Pharmacol.* 145:664-671.
Clayman "Contact Dermatitis Treated with Fludrocortisone: Steroid-Antibiotic Combination in the Inflammatory Dermatoses" 1958, *J. Med. Soc. New Jersey* 55(4):168-169.
Crabbe "Aldosterone: Mechanism of Action on Isolated Sodium-Transporting Epithelia" 1972, *J. Steroid Biochem.* 3(3):557-566.
Delcayre et al. "Molecular Mechanisms of Myocardial Remodeling. The Role of Aldosterone" 2002, *J. Mol. Cell. Cardiol.* 34:1577-1584.
Fardella et al. "Molecular Biology of Mineralocorticoid Metabolism" 1996, *Annu. Rev. Nutr.* 16:443-470.
Fuller et al. "Mechanisms of Mineralocorticoid Action" 2005, *Hypertension* 46:1227-1235.
Funder "Minireview: Aldosterone and Mineralocorticoid Receptors: Past, Present, and Future" 2010, *Endocrinology* 151:5098-5102.
Garrod "The Pharmacology of Cortisone, Cortisol (Hydrocortisone) and Their New Analogues" 1958, *Postgrad. Med. J.* 34:300-309.
Goodman et al. "The Pharmaceutical Basis of Therapeutics, 6th ed." 1980, *MacMillan Publishing Co., New York* (TOC).
Haseroth et al. "Rapid Nongenomic Effects of Aldosterone in Mineralcorticoid-receptor-knockout Mice" 1999, *Biochem. Biophys. Res. Comm.* 266:257-261.
He et al. "Oxidation of CaMKII determines the cardiotoxic effects of aldosterone" Dec. 2011, *Nature Medicine* 17(12):1610-1691.

(Continued)

*Primary Examiner* — Zachary Howard
(74) *Attorney, Agent, or Firm* — Pepper Hamilton LLP

(57) ABSTRACT

Compositions and methods for inducing the deposition of elastin by administering compositions including a mineralocorticoid, such as, for example, aldosterone and, optionally, a secondary active agent for enhancing or modulating the effect of the mineralocorticoid are described herein.

12 Claims, 30 Drawing Sheets
(11 of 30 Drawing Sheet(s) Filed in Color)

(56) References Cited

OTHER PUBLICATIONS

Hinek et al. "Decreased elastin deposition and high proliferation of fibroblasts from Costello syndrome are related to functional deficiency in the 67-Kd elastin-binding protein" 2000, *Am. J. Genet.* 66(3):859-872.

Hinek et al. "Impaired Elastic-Fiber Assembly by Fibroblasts from Patients with Either Morquio B Disease or Infantile GM1-Gangliosidosis Is Linked to Deficiency in the 67-Kd Spliced Variant of β-Galactosidase" 2000, *Am. Hum. Genet.* 67(1):23-36.

Hinek et al. "Impaired elastogenesis in Hurler disease: dermatan sulfate accumulation linked to deficiency in elastin-binding protein and elastic fiber assembly" 2000, *Am. J. Pathol.* 156(3):925-938.

Hinek et al. "Proteolytic digest derived from bovine Ligamentum Nuchae stimulates deposition of new elastin-enriched matrix in cultures and transplants of human dermal fibroblasts" 2005, *Dermatol. Sci.* 39(3):155-166.

International Search Report and Written Opinion dated Sep. 15, 2008 for PCT/US2008/066131.

Kenouch et al. "Human Skin as Target for Aldosterone: Coexpression of Mineralcorticoid receptors and 11 beta-hydroxysteroid Dehydrogenase" 1994, *J. Clin. Endrocrinol. Metab.* 79(5):1334-1341.

Lacolley et al. "Increased Carotid Wall Elastic Modulus and Fibronectin in Aldosterone-Salt-Treated Rates" 2002, *Circulation* 106:2848-2853.

Li et al. "Elastin Overexpression by Cell-based Gene Therapy Preserves Matrix and Prevents Cardiac Dilation" Mar. 21, 2012, *J. Cell Mol. Med.* [epub ahead of print].

Mill et al. "Spironactone Prevents Cardiac Collagen Proliferation After Myocardial Infarction in Rats" 2003, *Clin. Exper. Pharma. and Physiology* 30:739-744.

Mitts et al. "Aldosterone and Mineralocorticoid Receptor Antagonists Modulate Elastin and Collagen Deposition in Human Skin" Jun. 10, 2010, *Journal of Investigative Dermatology advance online publication* doi: 10.1038/jid.2010.155.

Mizuno et al. "Elastin Stabilizes an Infarct and Preserves Ventricular Function" 2005, *Circulation* 112(1):I-81-I-88.

Rosenbloom et al. "Extracellular matrix 4: The elastic fiber" 1993, *FASEB J.* 7:1208-1218.

Sharp et al. "Mechanism of Action of Aldosterone" 1966, *Physiol. Rev.* 46(4):593-633.

Ventura et al. "Effect of Chronic Oral Administration of a Low Dose of Captopril on Sodium Appetite of Hypothyroid Rats. Influence of Aldosterone" 2001, *Treatment, Braz J Med Biol Res* 34(3):407-411.

Vinson "The Mislabelling of Deoxycorticosterone: Making Sense of Corticosteroid Structure and Function" 2011, *J. Endocrinol.* 211:3-16.

Steady-state levels of Elastin mRNA

Deposition of Insoluble Elastin

Immunostaining with anti-Elastin Antibody

ALDOSTERONE INDUCED VASCULAR ELASTIN PRODUCTION

CROSS-REFERENCE TO RELATED APPLICATIONS

This application is a continuation application of U.S. application Ser. No. 12/937,534, filed Oct. 12, 2010, which is an application filed under 35 U.S.C. §371 of International Application No. PCT/US09/046,582, filed Jun. 8, 2009, which claims priority to U.S. Provisional Application No. 61/059,475, filed Jun. 6, 2008 and U.S. Provisional Application No. 61/059,288, filed on Jun. 6, 2008, all of which are herein incorporated by reference in their entirety.

GOVERNMENT INTERESTS

Not applicable

PARTIES TO A JOINT RESEARCH AGREEMENT

Not Applicable

INCORPORATION BY REFERENCE OF MATERIAL SUBMITTED ON A COMPACT DISC

Not Applicable

BACKGROUND

Not applicable

BRIEF SUMMARY OF THE INVENTION

Embodiments presented herein are useful for increasing elastogenesis in a post-infarct heart and scarred vasculature and thus, the such embodiments can counteract pathological fibrosis, as well as heart stiffness and/or and heart failure.

Embodiments presented herein include compositions for treatment of vascular tissues such as the heart with a mineralocorticoid and a secondary active agent selected from agents that reduce the net deposition of collagen, agents that increase the expression or sensitivity of insulin growth factor receptor I, and a combination thereof.

Various embodiments include a pharmaceutical composition including a therapeutically effective amount of mineralocorticoid and a pharmaceutically acceptable excipient.

Various other embodiments include methods for increasing the net deposition of elastin; such methods may include administering an effective amount of a mineralocorticoid to a subject in need thereof. In one embodiment, the mineralocorticoid aldosterone is used to stimulate elastogenesis in an MR-independent manner either alone or in combination with other agent wherein blocking MR coincides with elastic fiber production. In other embodiments, corticosteroids having at least some mineralocorticoid activity, such as, for example, deoxycorticosterone and fludrocortisones may be used.

Still other embodiments include a method for improving cardiac function, such methods may include administering a pharmaceutical composition at least including an effective amount of a mineralocorticoid and a pharmaceutically acceptable excipient to a subject in need thereof.

The methods disclosed herein maybe used to treat any condition such as alcoholic cardiomyopathy, coronary artery disease, congenital heart disease, nutritional diseases affecting the heart, ischemic cardiomyopathy, hypertensive cardiomyopathy, valvular cardiomyopathy, inflammatory cardiomyopathy, cardiomyopathy secondary to a systemic metabolic disease, dilated cardiomyopathy (DCM), hypertrophic cardiomyopathy (HCM), arrhythmogenic right ventricular cardiomyopathy (ARVC), restrictive cardiomyopathy (RCM), noncompaction cardiomyopathy, supravalvular aortic stenosis (SVAS), vascular scarring, atherosclerosis, chronic progressive glomerular disease, glomerulosclerosis, progressive renal failure, vascular occlusion, hypertension; stenosis, diabetic retinopathy, as well as any combination thereof.

DESCRIPTION OF DRAWINGS

The file of this patent contains at least one photograph or drawing executed in color. Copies of this patent with color drawing(s) or photograph(s) will be provided to the Patent and Trademark Office upon request and payment of the necessary fee.

For a fuller understanding of the nature and advantages of the present invention, reference should be made to the following detailed description taken in connection with the accompanying drawings.

DETAILED DESCRIPTION

Figure 1:
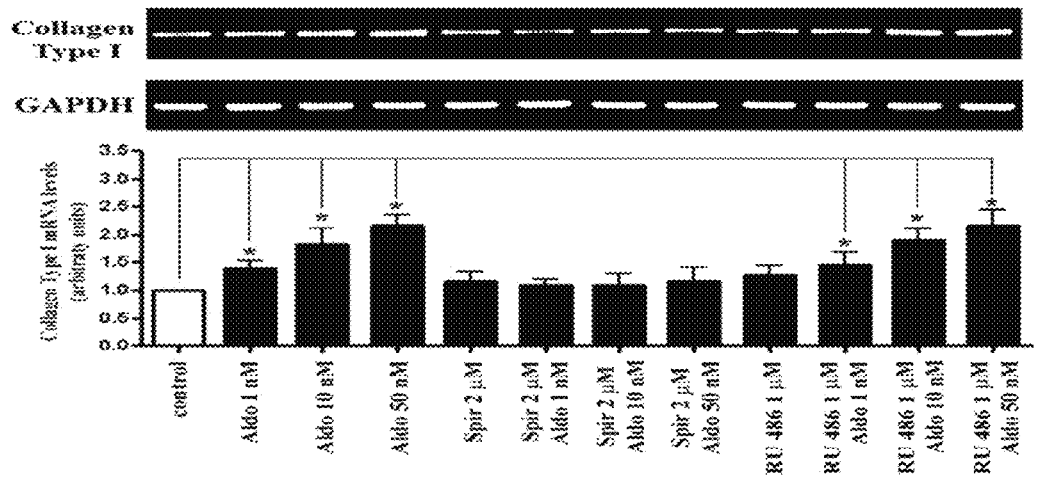
FIG. 1. The effect of aldosterone, the MR antagonist spironolactone, and the GR antagonist RU 486 on collagen type I production in cultures of human fetal cardiac fibroblast. A: A one-step RT-PCR analysis was used to assess collagen type I mRNA transcripts in cultures treated for 24 hours with or without 1 to 50 nmol/L aldosterone or pretreated for 1 hour with spironolactone or RU 486 and normalized to the corresponding levels of GAPDH mRNA transcripts. The results indicate that aldosterone treatment significantly increased collagen type I mRNA transcript levels compared with untreated control values (*$P<0.05$). Cells pretreated for 1 hour with spironolactone, before aldosterone treatment, returned the aldosterone-induced increase in collagen type I mRNA levels to untreated values, whereas RU 486 pretreatment had no effect on the aldosterone-induced increase in collagen type I mRNA transcript levels. B: Representative photomicrographs of confluent cultures immunostained with antibody to collagen I confirm the results presented in A. Fibroblasts were initially plated (100,000 cells/dish) and maintained in a normal medium until confluence. The cultures were then maintained for 72 hours with or without 1-50 nmol/L of aldosterone, in the presence or absence of spironolactone (2 µmol/L) or the glucocorticoid receptor antagonist RU 4861 (1 µmol/L).
Figure 1:
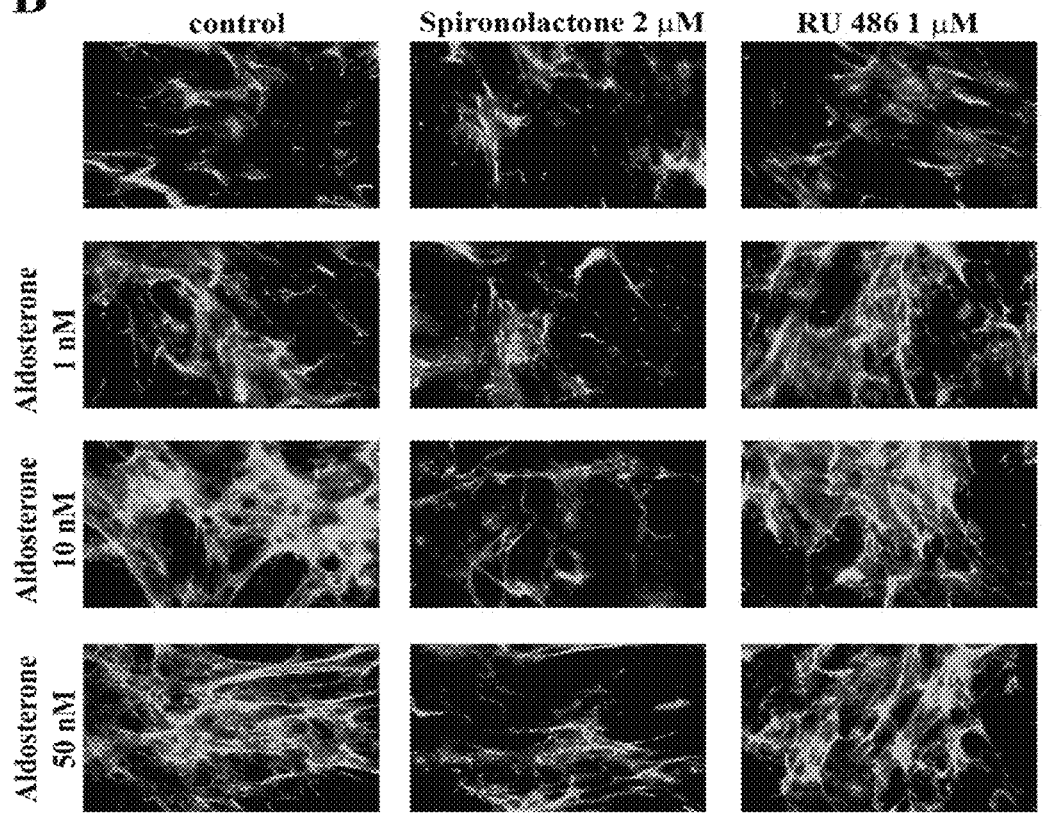

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must be noted that as used herein, and in the appended claims, the singular forms "a," "an," and "the" include plural reference unless the context clearly dictates otherwise. Thus, for example, reference to a "fibroblast" is a reference to one or more fibroblasts and equivalents thereof known to those skilled in the art.

As used herein, all claimed numeric terms are to be read as being preceded by the term, "about," which means plus or minus 10% of the numerical value of the number with which it is being used. Therefore, a claim to "50%" means "about 50%" and encompasses the range of 45%-55%.

"Administering" when used in conjunction with a therapeutic means to administer a therapeutic directly into or onto a target tissue, or to administer a therapeutic to a patient whereby the therapeutic positively impacts the tissue to which it is targeted. Thus, as used herein, the term "administering," when used in conjunction with aldosterone or any other composition described herein, can include, but is not limited to, providing aldosterone locally by administering aldosterone into or onto the target tissue, providing aldosterone systemically to a patient by, for example, intravenous injection whereby the therapeutic reaches the target tissue or providing aldosterone in the form of the encoding sequence thereof to the target tissue (e.g., by so-called gene-therapy techniques). "Administering" a composition may be accomplished by any mode including parenteral administration including injection, oral administration, topical administration, pleural infusion, pericardial infusion, or by any other method known in the art including for example electrical deposition (e.g., iontophoresis) and ultrasound (e.g., sonophoresis). In certain embodiments, the compositions described herein may be administered in combination with another form of therapy, including for example radiation therapy, infrared therapy, ultrasound therapy, or any other therapy know in the art or described herein.

In certain embodiments, the compositions may be combined with a carrier. A "carrier" as used herein may include, but is not limited to, an irrigation solution, antiseptic solution, other solution time released composition, elution composition, bandage, dressing, colloid suspension (e.g., a cream, gel, or salve) internal or external dissolvable sutures, dissolvable beads, dissolvable sponges and/or other materials or compositions known now or hereafter to a person of ordinary skill in the art.

The term "animal" as used herein includes, but is not limited to, humans and non-human vertebrates, such as wild, domestic, and farm animals.

The term "improves" is used to convey that the present invention changes either the appearance, form, characteristics and/or the physical attributes of the tissue to which it is being provided, applied or administered. The change in form may be demonstrated by any of the following, alone or in combination: enhanced deposition of elastin, increased elasticity of the cardiac tissue, reduced scar tissue formation, increased cardiac output or any other such improvement recognized in the art or described herein.

The term "inhibiting" includes the administration of a compound of the present invention to prevent the onset of the symptoms, alleviating the symptoms, or eliminating the disease, condition or disorder.

By "pharmaceutically acceptable," it is meant that the carrier, diluent or excipient must be compatible with the other ingredients of the formulation and not deleterious to the recipient thereof. By "excipient," it is meant any inert or otherwise non-active ingredient, which can be added to the active ingredient which may improve the overall composition's properties, such as improving shelf-life, improving retention time at the application site, improving flowability, improving consumer acceptance, et alia.

Unless otherwise indicated, the term "cardiac" means pertaining to the heart and related tissues. The term "vascular" encompasses cardiac tissue as well as any other blood bearing tissue, such as veins, arteries, capillaries, and others.

As used herein, the term "therapeutic" means an agent utilized to treat, combat, ameliorate, prevent or improve an unwanted condition or disease of a patient.

A "therapeutically effective amount" or "effective amount" of a composition is a predetermined amount calculated to achieve the desired effect, i.e., to increase production of elastin or the deposition of elastic fibers. For example, a therapeutic effect may be demonstrated by increased elastogenesis, increased cellular proliferation, increased digestion or resorption of scar material, reduction of symptoms and sequellae as well as any other therapeutic effect known in the art. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, the physical characteristics of the patient (height, weight, etc.), and the condition being treated. It will be understood that the effective amount administered will be determined by the physician in light of the relevant circumstances, including the condition to be treated, the choice of compound to be administered, and the chosen route of administration, and therefore, the dosage ranges provided are not intended to limit the scope of the invention in any way. A "therapeutically effective amount" of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Generally speaking, the term "tissue" refers to any aggregation of similarly specialized cells which are united in the performance of a particular function. As used herein, "tissue," unless otherwise indicated, refers to tissue which includes elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity.

The extracellular matrix (ECM) is made up of fibronectin, laminin, collagen and elastic fibers, as well as numerous glycosaminoglycans and protoglycans. These ECM components are organized into a network of rope-like structures which underlies many tissues, such as, blood vessels, skin, tendons, ligaments, and lungs. Of these ECM components, elastin is unique in that it can be stretched to over 150 percent of its original length and rapidly returns to its original size and shape. This property provides tissues in which elastin is incorporated with the ability to resume their original form after stretching. Therefore, elastin and elastin fibers allow these tissues to maintain the resiliency, stretchability and shape of these tissues.

Elastic fiber formation (elastogenesis) is a complex process involving intracellular and extracellular events. Cells such as fibroblasts, endothelial cells, chondroblasts or vascular smooth muscle cells, first synthesize and secrete glycoproteins that form a microfibrillilar scaffold into the extracellular space. Tropoelastin, the soluble precursor peptide of elastin, is synthesized in these cells by ribosomes in the rough endoplasmatic reticulum and transported through the Golgi apparatus and secretory vesicles that deposit tropoelastin in the extracellular space. Once outside the cell, tropoelastin is assembled into long chains and covalently cross-linked by lysyl oxidase. During crosslinking, unique composite amino acids, desmosine and isodesmosine, which join the tropoelastin chains, are formed and insoluble elastin is created.

Elastin fibers are composed of two major components: an amorphous, elastin core which makes up the bulk (>90%) of the fiber; and the 10-12 nm microfibrilary component surrounding the elastin core made up of glycoproteins, such as, for example, fibrillins, fibulins and microfibril-associated glycoproteins (MAGPs). Elastin may also be interwoven with non-elastic collagen fibers to limit stretching and prevent tearing of certain tissues. Mature (insoluble) elastin is metabolically inert and remains the most durable element of extracellular matrix. In undisturbed tissues, mature elastin may last for the lifetime of the tissue.

Deposition of elastin in the ECM appears to be controlled on both the transcriptional level (tropoelastin mRNA message expression) and post-transcriptional level (tropoelastin message stability). Other post-transcriptional events which control secretion of tropoelastin monomers, extracellular assembly of tropoelastin, and regulation of cross-linking of tropoelastin may also control elastin deposition.

The proper mechanical performance of the myocardium depends on the contractile properties of cardiac myocytes that are supported by the mechanical strength and resiliency of the extracellular matrix (ECM). Following myocardial injury, the cardiac ECM undergoes dynamic local remodeling, which leads to the production of scar tissue. However, overzealous ECM production in postinfarct hearts may lead to maladaptive fibrosis and contribute to heart failure.

Aldosterone is one of the major mediators involved in cardiac remodeling following cardiac stress and injury. It has been implicated in the maladaptive remodeling of postinfarct hearts. Its classic effect is attributed to mineralocorticoid receptor (MR)-mediated salt and fluid retention related to the regulation of blood pressure homeostasis. Aldosterone has also been implicated in the stimulation of collagen synthesis and myocardial fibrosis, through a process that is independent of its effect on blood pressure. It should also be noted that in vivo models of exogenous aldosterone administration produce an extensive MR-mediated cardiac pathology (fibrosis).

Even though cardiac fibrosis substantially contributes to cardiac dysfunction and arrhythmogenicity associated with sudden death, the role of various ECM components, including elastic fibers that provide resilience and elasticity to many tissues, including stroma of the heart, has not been adequately addressed.

It has been found that a mineralocorticoid receptor (MR)-independent pathway exists for stimulation of fibroblasts which involves at least at some point the IGF-IR receptor. This MR-independent pathway can be stimulated by mineralocorticoids such as aldosterone, which surprisingly will causes elastogenesis, not collagen deposition or salt uptake as when aldosterone binds the cognate mineralocorticoid receptor. Thus, by simultaneously down regulating the MR-dependent pathway, and upregulating the MR-independent pathway, it becomes possible to regulate both fibrosis (collagen deposition) and elastin production simultaneously.

Results disclosed herein show that although a MR antagonist inhibits or abolishes the collagenogenic effect of aldosterone, it does not eliminate the elastogenic effect of this hormone. In fact, pretreatment with spironolactone supports an aldosterone-induced increase in the net deposition of elastic fibers. This indicates that the beneficial cardioprotective effect of MR antagonist(s) may also be attributed to the deposition of new elastic fibers that may result in the formation of a resilient scar rather than a stiff collagenous scar that could hinder cardiac muscle contraction and relaxation, and further that mineralocorticoids can produce a cardioprotective effect if administered in conjunction with MR antagonists.

In certain embodiments, the concentration of aldosterone is in the range of 1-2 µM. In other embodiments, the concentration of spironolactone is in the range of 10-20 µM. However, these dosages may be adjusted since there is virtually no danger of a systemic overdose. As such, aldosterone (and any other mineralocorticoid equivalents such as deoxycorticosterone and fludrocortisones) may be administered, either alone or in combination with any other active agent, at 0.01 µM, 0.1 µM, 1.0 µM, 2.0 µM, 5.0 µM, 10.0 µM, 20.0 µM, 50 µM, 100 µM, and any range therebetween. Similarly, spironolactone (and any other mineralocorticoid receptor antagonists such as eplerenone and canrenone) may be administered at any suitable dose, either alone or in combination with another active agent such as aldosterone at 0.01 µM, 0.1 µM, 1.0 µM, 2.0 µM, 5.0 µM, 10 µM, 20 µM, 50 µM, 100 µM, 200 µM and any range therebetween. Those of ordinary skill in the art recognize that such dosages can be calculated per liter of compound. Whatever route of administration or type of pharmaceutical dosage form is used, the dosage range can be from about 0.5 to about 30 mg/kg of patient body weight or about 350 to about 2,000 mg, and about 500 to about 1,500 mg, although dosage amounts towards the lower end of these range would be useful for parenteral administration. See also, U.S. Provisional Patent Application 60/943,305 filed Jun. 6, 2007, PCT Application No. U.S. Ser. No. 08/066,131 filed Jun. 6, 2008 and U.S. application Ser. No. 12/157,141 filed on Jun. 6, 2008, each of which are herein incorporated by reference in their entirety.

Embodiments presented herein are generally directed to compositions including at least one mineralocorticoid and methods of using such compositions for the treatment of tissue.

The composition of various embodiments may include any mineralocorticoid known in the art, including, for example, aldosterone. Other embodiments include pharmaceutical compositions, including a mineralocorticoid and a pharmaceutically acceptable carrier, diluent, or excipient, and in certain embodiments, the compositions or pharmaceutical compositions may include secondary active agents which enhances or improves the function of the mineralocorticoid. Such compositions may be formulated in any way. For example, in various embodiments, the compositions may be formulated as a liquid, solid, gel, lotion or cream, and the formulation of the composition may vary among embodiments depending on the mode of administration of the compositions.

In some embodiments, corticosteroids having at least some mineralocorticoid activity, such as, for example, deoxycorticosterone and fludrocortisones may be used in place of or in combination with the mineralocorticoids of the compositions and pharmaceutical compositions described above. Without wishing to be bound by theory, such corticosteroids may affect tissue treated therewith in the same manner as mineralocorticoids, such as aldosterone.

In various embodiments, the mineralocorticoid may interact with cells, such as, for example, fibroblasts and the like, and induce the production of elastin by these cells or increase the deposition of the elastin into the extracellular space surrounding these cells. In certain embodiments, aldosterone may interact with such cells in a mineralocorticoid receptor (MR) independent manner. Thus, in some embodiments, aldosterone may be administered in combination with a secondary active agent. As used herein the term secondary active agent is intended to mean a pharmacologically active compound administered in conjunction with a mineralocorticoid. As such, in certain embodiments, secondary active agent include those that inhibits collagen synthesis by inhibiting MR stimulation or deposition associated with MR stimulation, reduces the synthesis or deposition of collagen in activated cells, inhibiting factors associated with collagen synthesis or factors associated with collagen deposition and combinations of these, while maintaining or enhancing production of elastin or elastin fibers. Without wishing to be bound by theory, inhibition of collagen synthesis or deposition of collagen may enhance the effectiveness of various embodiments by producing a net increase in deposition of elastin fibers while reducing the net deposition of collagen which may be associated with, for example, scar tissue. Therefore, in some embodiments, aldosterone may be administered in combination with an agent that inhibits MR activation or collagen synthesis associated with MR stimulation or inhibits collagen synthesis throughout effected cells. For example, in an embodiment, aldosterone may be administered in combination with mineralocorticoid receptor antagonist such as eplerenone, canrenone, spirolactone et alia, which are synthetic lactone drugs that act as a competitive aldosterone antagonist. In yet another embodiment, a mineralocorticoid such as aldosterone may be administered in combination with an MR binding antibody, such as, for example, mineralocorticoid receptor antibody (H10E4C9F) mineralocorticoid receptor antibody (H3122), Mouse Anti-Human NR3C2 Monoclonal Antibody (Clone 2B5), Mouse Anti-Human Mineralocorticoid R (aa 1-670 Clone 385707), et alia disclosed herein or described in the art.

The mineralocorticoid, or aldosterone, of various embodiments may interact with cells, such as, for example, fibroblasts in an insulin growth factor receptor I (IGF-IR) dependent manner. Therefore, in some embodiments, aldosterone may be administered in combination with an agent that enhances the pro-elastogenic effect of IGF-IR stimulation or stimulates the synthesis of IGF-IR, IGF-IR kinase, or other components of the IGF-IR signaling pathway and combinations thereof. Without wishing to be bound by theory, enhancing the ability of a cell to be stimulated by aldosterone by increasing the expression of IGF-IR or the sensitivity of IGF-IR on the cell surface may increase the net deposition of elastin fibers in treated tissue thereby enhancing the effectiveness of such treatment. By "increased expression," it is intended to mean an effect on any pathway that leads to an increase of the number of functional protein molecules, and includes for example, increased IGF-IR mRNA synthesis, increased IGF-IR mRNA stability, increased anabolism of the protein, decreased catabolism of the protein, and any other pathway by which expression can be increased. By "increased sensitivity," it is intended to mean increasing the responsiveness of the protein to its ligand, which can occur in any manner including crosslinking of receptors, conformational changes in the receptors, phosphorylation/dephosphorylation of the receptor, or any other mechanism by which sensitivity can be increased.

The compositions described in the embodiments above may be administered to any tissue in need of enhanced elastin deposition. For example, in some embodiments, such compositions may be administered to ischemic vascular tissues including cardiac tissue, scarred vascular tissues including cardiac tissue, growing and or/regrowing vascular tissues including cardiac tissue. In other embodiments, the composition may be administered to cells and tissues associated with trauma or excessive collagen formation.

In embodiments wherein aldosterone is administered in combination with a secondary active agent, the combination may be administered as a single unit wherein the aldosterone and secondary active agent are combined to form a single, tablet or injectable emulsion, for example. In other embodiments, aldosterone may be administered separately from the secondary active agent, and in particular embodiments, the one component may be administered at a separate time from the other component. For example, in one embodiment, the secondary active agent may be administered first to prepare the target tissue by, for example, increasing IGF-IR expression, and aldosterone may be administered at a later time.

Methods of embodiments generally include administering a composition or pharmaceutical composition including a mineralocorticoid to a subject or patient in need of treatment. Pharmaceutical compositions useful in various embodiments may be administered to treat, ameliorate, or alleviate symptoms associated with various diseases that may be identified by inability to produce elastin or elastin fibers, or functional elastin or elastin fibers, loss of functional elastin or elastin fibers, or the lack or loss of deposition of elastin or elastin fibers in the subject's tissue. Such diseases include alcoholic cardiomyopathy, coronary artery disease, congenital heart disease, nutritional diseases affecting the heart, ischemic cardiomyopathy, hypertensive cardiomyopathy, valvular cardiomyopathy, inflammatory cardiomyopathy, cardiomyopathy secondary to a systemic metabolic disease, dilated cardiomyopathy (DCM), hypertrophic cardiomyopathy (HCM), arrhythmogenic right ventricular cardiomyopathy (ARVC), restrictive cardiomyopathy (RCM), noncompaction cardiomyopathy, supravalvular aortic stenosis (SVAS), as well as vascular scarring diseases including atherosclerosis, chronic progressive glomerular disease, (e.g., diabetic-induced glomerulosclerosis), progressive renal failure after renal transplantation, occlusion of shunts used to provide vascular access in patents with end stage renal disease being treated with hemodialysis, other chronic small blood vessel diseases (such as in some patients with hypertension), recurrence of stenosis in patients who have undergone coronary bypass surgery, diabetic retinopathy and any combination thereof.

In certain embodiments, a method of administering an effective amount of aldosterone in a patient in need thereof is described. Yet in another embodiment, the method of treating cardiac dysfunction by administering an effective amount of aldosterone in a patient in need thereof is described. Additionally, the method of administering an effective amount of aldosterone in a patient in need thereof is to improve the ejection fraction in a heart of a patient in need thereof.

Various embodiments, therefore, include pharmaceutical compositions having a mineralocorticoid or combination of a mineralocorticoid and a secondary active agent of embodiments described above, and a pharmaceutically acceptable carrier, diluent or excipient, or an effective amount of a pharmaceutical composition including a mineralocorticoid or combination of a mineralocorticoid and a secondary active agent, as defined above, and a pharmaceutically acceptable carrier, diluent or excipient.

The compounds of the various embodiments may be administered in a conventional manner by any route by which they retain activity. For example, a mineralocorticoid or combination of a mineralocorticoid and a secondary active agent of embodiments may be administered by routes including, but not limited to, topical, parenteral, pleural, pericardial, subcutaneous, intravenous, intraperitoneal, transdermal, oral, buccal, inhalation, depot injection, or implantation. Thus, modes of administration for the compounds (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal and topical forms such as patches and creams.

Specific modes of administration will depend on the indication and other factors including the particular compound being administered. The selection of the specific route of administration and the dose regimen is to be adjusted or titrated by the clinician according to methods known to the clinician in order to obtain the optimal clinical response. In still other embodiments, the compositions may be administered both systemically and topically.

The amount of the compositions of various embodiments to be administered is an amount that is therapeutically effective, and the dosage administered may depend on the characteristics of the subject being treated. For example, the dosage may depend on the particular animal treated, the age, weight, and health of the subject, the types of concurrent treatment, if any, and frequency of treatments. Many of these factors can be easily determined by one of skill in the art (e.g., by the clinician).

Various pharmaceutical formulations include those containing an effective amount the compounds and a suitable carrier, diluent, or excipient can be in solid dosage forms including, but not limited to, tablets, capsules, cachets, pellets, pills, powders and granules; topical dosage forms including, but not limited to, solutions, powders, fluid emulsions, fluid suspensions, semi-solids, ointments, pastes, creams, lotions, gels, jellies, and foams; and parenteral dosage forms including, but not limited to, solutions, suspensions, emulsions, and dry powders. The active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like.

The means and methods for administration of such pharmaceutical formulations are known in the art and an artisan can refer to various pharmacologic references, such as, for example, *Modern Pharmaceutics*, Banker & Rhodes, Marcel Dekker, Inc. (1979) and *Goodman & Gilman's The Pharmaceutical Basis of Therapeutics,* 6th Edition, MacMillan Publishing Co., New York (1980) for guidance. For example, in some embodiments, the compounds can be formulated for parenteral administration by injection, and in one embodiment, the compounds can be administered by continuous infusion subcutaneously over a period of about 15 minutes to about 24 hours. In another embodiment, formulations for injection can be presented in unit dosage form, e.g., in ampoules or in multi-dose containers, with an added preservative. In still other embodiments, the compositions can take such forms as suspensions, solutions or emulsions in oily or aqueous vehicles, and can contain formulatory agents such as suspending, stabilizing and/or dispersing agents.

For certain embodiments encompassing oral administration, the compounds can be formulated readily by combining these compounds with pharmaceutically acceptable carriers known in the art. Such carriers enable the compounds to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers. If desired, disintegrating agents, such as, but not limited to, the cross-linked polyvinyl pyrrolidone, agar, or alginic acid or a salt thereof, such as sodium alginate, may be added.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally also include, but are not limited to, push-fit capsules made of gelatin, as well as soft, sealed capsules made of gelatin and a plasticizer, such as glycerol or sorbitol. The push-fit capsules can contain the active ingredients in a mixture with filler such as binders and/or lubricants, such as, for example, talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, for example, tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions, such as, suppositories or retention enemas, for example, containing conventional suppository bases such as cocoa butter or other glycerides.

In addition to the formulations described previously, the compounds of the present invention can also be formulated as a depot preparation. Such long acting formulations can be administered by implantation (for example, subcutaneously, intramuscularly or intracardialy) or by direct injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

In transdermal administration, the compounds of the present invention can, for example, be applied to a plaster, or can be applied by transdermal, therapeutic systems that are consequently supplied to the organism.

Pharmaceutical compositions of the compounds also can include suitable solid or gel phase carriers or excipients. Examples of such carriers or excipients include but are not limited to calcium carbonate, calcium phosphate, gelatin, and polymers such as, for example, polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

In one embodiment, a composition for treatment of cardiac damage comprising:
  a mineralocorticoid; and a second active agent selected from the group consisting of agents that reduce the net deposition of collagen, agents that increase the expression or sensitivity of insulin growth factor receptor I, and combinations thereof is described.

In certain embodiments, the mineralocorticoid increases the net deposition of elastin in a heart.

Yet in another embodiment, the mineralocorticoid increases the net deposition of elastin in a mineralocorticoid receptor independent manner.

In selected embodiments, the mineralocorticoid is selected from aldosterone, fludrocortisones, and deoxycorticosterone.

In one embodiment, the secondary active agent is selected from inhibitors of mineralocorticoid receptors, inhibitors of mineralocorticoid receptor stimulation, inhibitors of collagen synthesis, inhibitors of collagen deposition, inhibitors of factors associated with collagen synthesis, inhibitors of factors associated with collagen deposition, and combinations thereof.

In certain embodiments, the secondary active agent is selected from the group consisting of spironolactone and mineralocorticoid receptor neutralizing antibodies. Additionally, in another embodiment, the secondary active agent is selected from the group consisting of agents that stimulate synthesis of insulin growth factor receptor I, agents that stimulate synthesis of insulin growth factor receptor I kinase, agents that stimulate components of the insulin growth factor receptor I signaling pathway, and combinations thereof.

In another embodiment, a pharmaceutical composition comprising: a mineralocorticoid in an amount sufficient increase elastin production by cardiac fibroblasts to a subject in need thereof; and a pharmaceutically acceptable excipient is described.

Yet in another embodiment, the mineralocorticoid increases the net deposition of elastin in a heart. In another embodiment, the mineralocorticoid is selected from the group consisting of aldosterone, fludrocortisones, and deoxycorticosterone.

In another embodiment, the pharmaceutical composition is formulated to be administered by a mode selected from the group consisting of topical, parenteral, plural infusion, pericardial infusion, subcutaneous, intravenous, intraperitoneal, transdermal, oral, buccal, inhalation, depot injection, and implantation.

In another embodiment, the composition further comprises a collagen inhibitor.

In another embodiment, the collagen inhibitor reduces the net deposition of collagen in a heart. In other embodiments, the collagen inhibitor is selected from the group consisting of inhibitors of mineralocorticoid receptors, inhibitors of mineralocorticoid receptor stimulation, inhibitors of collagen synthesis, inhibitors of collagen deposition, inhibitors of factors associated with collagen synthesis, inhibitors of factors associated with collagen deposition, and combinations thereof. Additionally, in certain embodiments, collagen inhibitor of the pharmaceutical composition is selected from the group consisting of spironolactone and mineralocorticoid receptor neutralizing antibodies.

In another embodiment, the pharmaceutical composition, further comprising an agent that increases the expression or sensitivity of insulin growth factor receptor I.

In another embodiment, the agent in the pharmaceutical composition is selected from the group consisting of agents that stimulate synthesis of insulin growth factor receptor I, agents that activate insulin growth factor receptor I, agents that stimulate synthesis of insulin growth factor receptor I kinase, agents that stimulate components of the insulin growth factor receptor I signaling pathway, and combinations thereof.

Further embodiment of the present invention encompasses a method for increasing the net deposition of elastin in a heart comprising administering a composition comprising an effective amount of a mineralcorticoid to a subject, a polypeptide fragment as disclosed in U.S. application Ser. No. 10/778,253 filed on Feb. 13, 2004, U.S. application Ser. No. 11/435,563 filed on May 17, 2006, U.S. Application No. 60,575,737 filed on May 28, 2004, U.S. application Ser. No. 11/394,345 filed on Mar. 29, 2006 and U.S. application Ser. No. 11/405,843 filed on Apr. 17, 2006, which are all incorporated by reference therein, and combinations thereof. In certain embodiments, a mineralcorticoid is aldosterone.

In one embodiment, a method for increasing the net deposition of elastin in a heart comprising administering a composition comprising an effective amount of a mineralcorticoid to a subject, a polypeptide fragment comprising VGAMPG (SEQ ID NO. 1), VGLSPG (SEQ ID NO. 2), IGAMPG (SEQ ID NO. 3), and IGLSPG (SEQ ID NO. 4), and combinations thereof is described. In certain embodiments, a mineralcorticoid is aldosterone.

This invention and embodiments illustrating the method and materials used may be further understood by reference to the following non-limiting examples.

EXAMPLES

In vitro studies described herein employed cultures of human cardiac fibroblasts.

Materials and Methods

All chemical-grade reagents, aldosterone, spironolactone, doxycycline, RU 486 (mifepristone), proteinase inhibitors, agarose-linked protein A, pertussis toxin, recombinant human insulin-like growth factor-I (IGF-I), insulin-like growth factor receptor-I (IGF-IR) inhibitor AG 1024, epidermal growth factor receptor (EGFR) inhibitor AG 1478, platelet-derived growth factor receptor inhibitor AG 1295, and transforming growth factor β receptor inhibitor SB 431542 were obtained from Sigma (St. Louis, Mo.). Iscove's modified Dulbecco's medium, fetal bovine serum, 0.2% trypsin-0.02% ethylenediamine tetraacetic acid, and other cell culture products were acquired from Gibco Life Technologies (Burlington, ON, Canada). Polyclonal antibody to tropoelastin was purchased from Elastin Products (Owensville, Mich.). Polyclonal collagen type I antibody was purchased from Chemicon (Temecula, Calif.). Monoclonal antibody against phosphotyrosine (PY99) and polyclonal antibody against IGF-IR were obtained from Santa Cruz Biotechnology (Santa Cruz, Calif.). IGF-IR-blocking monoclonal antibody was purchased from EMD Biosciences (San Diego, Calif.). Fluorescein-conjugated goat anti-rabbit and fluorescein-conjugated rabbit anti-goat secondary antibodies were purchased from Sigma and Chemicon, respectively. Species- and type-specific secondary antibodies conjugated to horseradish peroxidase, an enhanced chemiluminescence kit, and the radiolabeled reagent [$^3$H]valine were purchased from Amersham Biosciences Canada, Ltd. (Oakville, ON, Canada). A DNeasy tissue system for DNA assay and an RNeasy Mini Kit for isolating total RNA were purchased from Qiagen (Mississauga, ON, Canada), as well as a One-Step RT-PCR Kit. Bovine serum albumin-conjugated aldosterone (aldo-BSA) was purchased from Fitzgerald Industries Int. (Concord, Mass.); as specified by the manufacturer, 25 aldosterone molecules are covalently linked to each BSA molecule through a carboxymethyl oxime residue on the C3 of the hormone, forming a stable conjugate.

Cultures of Human Cardiac Fibroblasts

Cardiac fibroblasts were isolated from human fetal hearts (which are responsible for the production of cardiac ECM). Human fetal cardiac fibroblasts of 20 to 22 weeks of gestation were prepared in accordance with an Institutional Review Board-approved protocol. Confluent cultures were passaged by trypsinization and maintained in Iscove's modified Dulbecco's medium supplemented with 1% antibiotics/antimycotics and 10% fetal bovine serum. Passage 1 to 3 cells were used in all experiments. The purity of these cultures at passage 1 was 95%. Cardiac fibroblasts were identified by positive staining for vimentin and negative for von Willebrand factor and -smooth muscle cell actin.

In experiments aimed at assessing ECM production, fibroblasts were initially plated (100,000 cells/dish) and maintained in a normal medium until confluence, the point at which they produce abundant ECM. Confluent cultures were then treated for 72 hours with or without 1 to 50 nmol/L aldosterone.

In separate experiments the influence of an equimolar concentration of aldosterone was tested by coupling it to BSA which prevents it from penetrating into the cell interior. The aldosterone receptor antagonist spironolactone, the glucocorticoid receptor antagonist RU 486, and the following IGF-IR, EGFR, platelet-derived growth factor receptor, and transforming growth factor β receptor inhibitors AG 1024, AG 1478, AG 1295, and SB 431542, respectively, as well as the G-protein inhibitor pertussis toxin and the protein kinase C inhibitor staurosporine, and IGF-IR-neutralizing antibody were added 1 hour before aldosterone treatment. Control cell cultures received an equal amount of the solvent vehicle. To eliminate the possibility that the observed effects were restricted to the fetal cardiac fibroblasts, the influence of aldosterone on elastogenesis in cultures of commercially available adult human cardiac fibroblasts was also tested. ScienCell (San Diego, Calif.).

Immunostaining

At the end of the 72-hour incubation period with the indicated treatment, confluent cultures were either fixed in ice-cold 100% methanol at −20° C. (for elastin staining) or in 4% paraformaldehyde at room temperature (for collagen staining) for 30 minutes and blocked with 1% normal goat serum for 1 hour at room temperature. The cultures were then incubated for 1 hour with 10 µg/ml polyclonal antibody to tropoelastin or with 10 µg/ml polyclonal antibody to collagen type I. All cultures were then incubated for an additional hour with fluorescein-conjugated goat anti-rabbit or with fluorescein-conjugated rabbit anti-goat secondary antibodies to detect elastin and collagen type I staining, respectively. Nuclei were counterstained with propidium iodide. Secondary antibody alone was used as a control. All of the cultures were then mounted in Elvanol and examined with a Nikon Eclipse E1000 microscope attached to a cooled charge-coupled device camera (Retiga EX; QImaging, Surrey, BC, Canada) and a computer-generated video analysis system (Image-Pro Plus software; Media Cybernetics, Silver Spring, Md.).

Quantitative Assays of Tropoelastin and Insoluble Elastin

Fetal human cardiac fibroblasts were grown to confluence in 35-mm culture dishes (100,000 cells/dish) in quadruplicate. Then 2 µCi of [$^3$H]valine/ml of fresh media were added to each dish along with or without 1 to 50 nmol/L aldosterone in the presence and absence of spironolactone. Cultures were incubated for 72 hours, and the soluble and insoluble elastin were assessed separately in each dish. The cells were extensively washed with phosphate-buffered saline, and the soluble proteins present in the intracellular compartments were extracted overnight at 4° C. with 0.1 mol/L acetic acid in the presence of proteinase inhibitors. After centrifugation, the supernatants were precleaned by 30-minute incubation with 50 µl of 4% protein A-beaded agarose, and then 500 µl of the supernatant was incubated with 5 µg of polyclonal antibody to tropoelastin for 2 hours and subsequently with 50 µl of 4% protein A-beaded agarose for 3 hours at 4° C. The protein A-containing beads were sedimented by centrifugation, washed with immunoprecipitation buffer, mixed with scintillation fluid, and counted. The remaining cultures containing cell remnants and deposited insoluble extracellular matrix were scraped and boiled in 500 µl of 0.1 N NaOH for 30 minutes to solubilize all matrix components except elastin. The resulting pellets containing the insoluble elastin were then solubilized by boiling in 200 µl of 5.7 N HCl for 1 hour, and the aliquots were mixed in scintillation fluid and counted. Aliquots taken from each culture were also used for DNA determination according to Rodems and Spector, using the DNeasy Tissue System from Qiagen. Final results reflecting amounts of metabolically labeled insoluble elastin in individual cultures were normalized per their DNA content and expressed as counts per minute per 1 µg of DNA. In separate experiments the specified treatments as shown in the figure legends for FIGS. 2, 4, and 5 were added along with 2 µCi of [3H]valine/ml media to normal human skin fibroblasts grown to confluence in 35-mm culture dishes (100,000 cells/dish) in quadruplicate for 72 hours. The conditioned media were then removed, the cell layers were washed, and the incorporation of [$^3$H]valine into the insoluble elastin was assessed as described above.

One-Step Reverse Transcriptase-Polymerase Chain Reaction (RT-PCR) Analysis

Confluent fetal human cardiac fibroblast cultures were treated with or without the specified treatment shown in the figure legends for FIGS. 1 to 5 for 24 hours. Total RNA was extracted using the RNeasy Mini Kit according to the manufacturer's instructions, 1 µg of total RNA was added to each one-step RT-PCR (Qiagen One-Step RT-PCR Kit), and reactions were set up according to the manufacturer's instructions in a total volume of 25 µl. The reverse transcription step was performed for elastin and glyceraldehyde-3-phosphate dehydrogenase (GAPDH) reactions at 50° C. for 30 minutes, followed by 15 minutes at 95° C. The elastin PCR reaction (sense primer: 5' GGTGCGGTGGTTCCTCAGCCTGG-3; antisense primer: 5'-GGGCCTTGAGATAC-CCCAGTG-3; designed to produce a 255-bp product) was performed under the following conditions: 25 cycles at 94° C. denaturation for 20 seconds, 63° C. annealing for 20 seconds, 72° C. extension for 1 minute, and one cycle at 72° C. final extension for 10 minutes. The collagen type I PCR reaction (sense primer: 5'-CCCACCAATCACCTGCGTACAGA-3'; antisense primer: 5'-TTCTTGGTCGGTGGGTGACTCTGA-3') was performed under the following conditions: 20 cycles at 94° C. denaturation for 30 seconds, 58° C. annealing for 30 seconds, 72° C. extension for 10 minutes, and one cycle at 72° C. final extension for 10 minutes. The GAPDH PCR reaction (sense primer: 5'-TCCACCACCCTGTTGCTGTAG-3'; antisense primer: 5'-GACCACAGTCCATGCCATCACT-3; designed to produce a 450-bp product) was performed under the following conditions: 21 cycles at 94° C. denaturation for 20 seconds, 58° C. annealing for 30 seconds, 72° C. extension for 1 minute, and one cycle at 72° C. final extension for 10 minutes. Five-microliter samples of the elastin and GAPDH PCR products from each reaction were run on a 2% agarose gel and poststained with ethidium bromide. The amount of elastin mRNA was standardized relative to the amount of GAPDH mRNA.

Immunoprecipitation

Figure 6A:
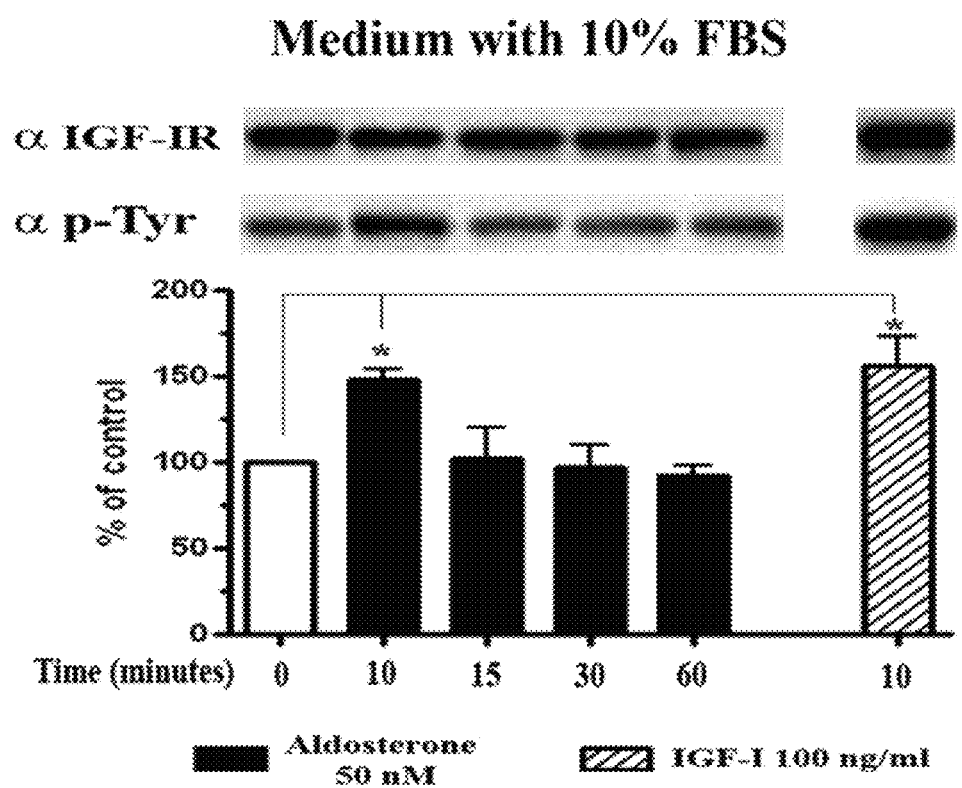
FIG. 6. Aldosterone rapidly increases tyrosine phosphorylation of the IGF-IR in fibroblast cultures via facilitation. Cardiac fibroblast cultures were treated with or without 50 nmol/L aldosterone for 0, 10, 15, 30, and 60 minutes or 100 ng/ml IGF-I for 10 minutes in the presence of 10% fetal bovine serum (A) or in the absence of serum (B) or in the absence of serum for 10 minutes (C) in the presence or absence of 10, 25, or 50 ng/ml IGF-I alone or with 50 nmol/L aldosterone. Cell lysates were immunoprecipitated (IP) with an IGF-IR antibody, electrophoresed, and probed with an anti-phosphotyrosine (α p-Tyr) antibody or anti-IGF-IR (αIGF-IR) antibody. Graphs depict the mean±SD of data from three individual experiments expressed as a percentage of control phosphorylation values obtained by normalizing to the corresponding total level of IGF-IR. Data in A and B demonstrate that a 10-minute aldosterone exposure in cultures maintained in 10% fetal bovine serum leads to a significant increase in tyrosine phosphorylation of IGF-IR over basal levels, similar to the effect observed after a 10-minute IGF-I treatment. *Statistically different from control group (P<0.05). Data in C demonstrate that cultures treated together with 50 nmol/L aldosterone and 10, 25, or 50 ng/ml IGF-I exhibit higher levels of IGF-IR tyrosine phosphorylation than their respective counterparts treated with the same doses of IGF-I alone. *, , and *, statistically different from the 10, 25, and 50 ng/ml IGF-I-treated group (P<0.05), respectively.
Figure 6B:
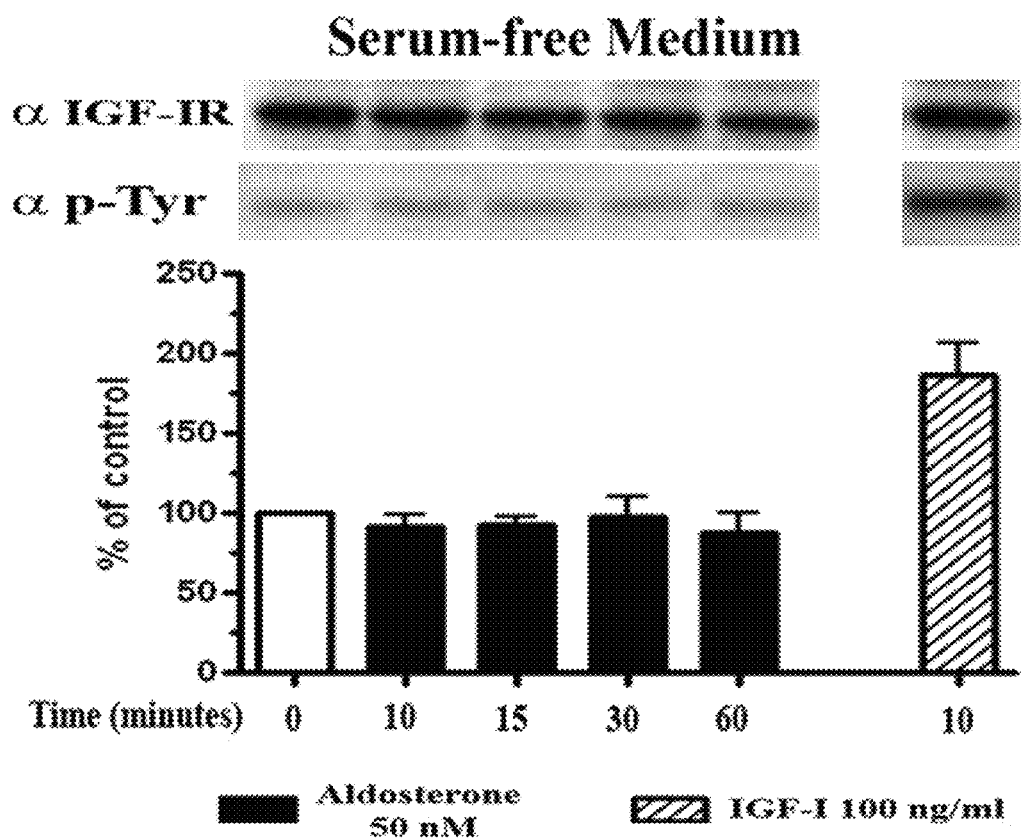

Confluent fetal human cardiac fibroblast cultures were incubated for the indicated time in the presence or absence of 50 nmol/L aldosterone or for 10 minutes with 100 ng/ml IGF-I, as specified in the figure legend for FIG. 6. Parallel cultures were incubated in serum-free conditions in the presence or absence of 50 nmol/L aldosterone and incubated with or without 10, 25, and 50 ng/ml IGF-I for 10 minutes. Cells were lysed using an radioimmunoprecipitation assay buffer [50 mmol/L Tris-HCl, pH 7.4, 150 mmol/L NaCl, 1 mmol/L ethylenediamine tetraacetic acid, 10 mmol/L NaF, 1% Triton X-100, 0.1% sodium dodecyl sulfate, 1% sodium deoxycholate containing a cocktail of antiproteases (20 µg/ml leupeptin, 10 µg/ml aprotinin, 0.1 mmol/L phenylmethylsulfonyl fluoride, and 1 mmol/L dithiothreitol) and antiphosphates (200 mol/L orthovanadate and 2 µg/ml pepstatin)], and 300 µg of protein extract was incubated with an antibody against IGF-IRβ for 1 hour at 4° C., followed by the addition of 4% protein A-beaded agarose left overnight, as previously described. The resulting protein-antibody conjugate was centrifuged at 4° C. and washed four times with phosphate-buffered saline. The final pellet was resuspended in sample buffer (0.5 mol/L Tris-HCl, pH 6.8, 10% sodium dodecyl sulfate, 10% glycerol, 4% 2-B-mercaptoethanol, and 0.05% bromphenol blue), and the mixture was boiled for 5 minutes. Proteins were resolved by 12% sodium dodecyl sulfate-polyacrylamide gel electrophoresis, transferred to nitrocellulose membranes, and then immunoblotted with anti-p-Tyr or anti-IGF-IR antibodies. The degree of expression or phosphorylation of immunodetected signaling molecules was measured by densitometry.

Data Analysis

In all biochemical studies, quadruplicate samples in each experimental group were assayed in three separate experiments. Mean and standard deviations were calculated for each experimental group, and statistical analyses were performed by analysis of variance. A P value of less than 0.05 was considered significant Example 1

Aldosterone Up-Regulates Collagen Type I Gene Expression and the Deposition of Collagen Fibers in an MR-Dependent Manner in Cultures of Cardiac Fibroblasts It was first demonstrated that treatment of cultured human fetal cardiac fibroblasts with 1 to 50 nmol/L aldosterone leads to a significant increase in the steady-state level of collagen type I mRNA and to the subsequent deposition of collagen fibers (FIG. 1). Then we found that pretreating cardiac fibroblasts with the MR-antagonist spironolactone but not with the glucocorticoid receptor (GR) antagonist RU 486 (1 µmol/L), abrogated aldosterone-induced collagen production (FIG. 1).

These results strongly indicate that the stimulatory effect of aldosterone on collagen production is mediated via MR activation.

Example 2

Figure 2A:
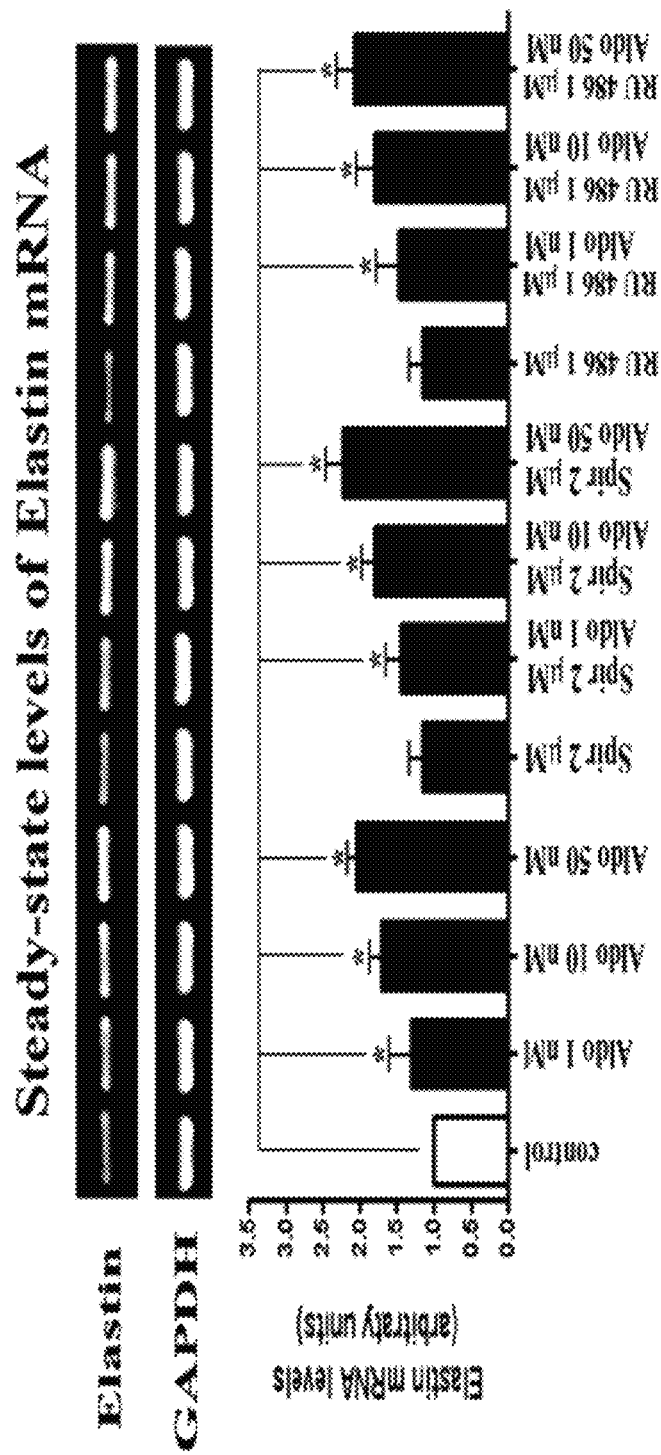
FIG. 2. The effect of aldosterone, the MR antagonist spironolactone, and the GR antagonist RU 486 on elastin production in cultures of human fetal cardiac fibroblasts. A: A one-step RT-PCR analysis was used to assess elastin mRNA transcripts in cultures treated for 24 hours with or without 1 to 50 nmol/L aldosterone or pretreated for 1 hour with spironolactone or RU 486 and normalized to the corresponding levels of GAPDH mRNA transcripts. The results demonstrate that aldosterone dose-dependently increased elastin mRNA transcript levels compared with untreated control values (*$P<0.05$) and that neither spironolactone nor RU 486 eliminated this increase. B: Results of a quantitative assay of newly produced, metabolically labeled, and immunoprecipitatable soluble tropoelastin demonstrate that cultures treated for 72 hours with 1 to 50 nmol/L aldosterone synthesize up to approximately three times more [$^3$H]valine-labeled tropoelastin than untreated counterparts (*$P<0.05$). The addition of spironolactone to aldosterone-treated cultures did not abrogate the increase in tropoelastin production. C: Results of a quantitative assay of insoluble elastin after metabolic labeling with [$^3$H]valine demonstrate that cells treated for 72 hours with 1 to 50 nmol/L aldosterone incorporate significantly more [$^3$H]valine into extracellular insoluble elastin compared with untreated cells (*P<0.05). Pretreating the cells with spironolactone for an hour before aldosterone exposure did not eliminate the increase in insoluble elastin production. D: Representative photomicrographs of confluent cultures immunostained with anti-elastin antibody confirm the results presented in C. Results of biochemical assays are expressed as the mean±SD, as derived from three separate experiments in which each experimental group had quadruplicate cultures.
Figure 2B:
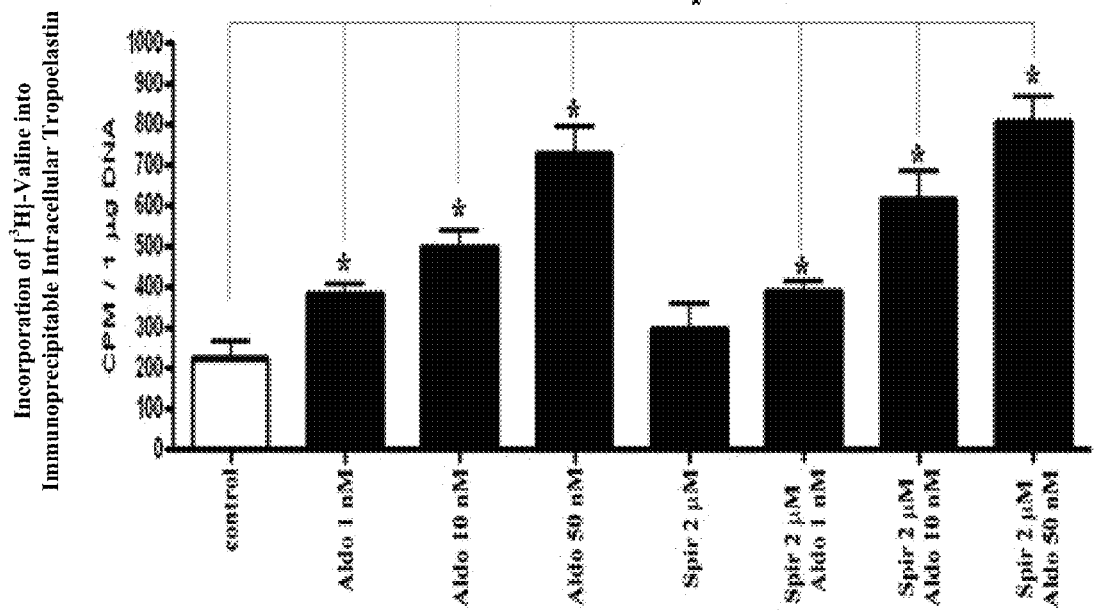
Figure 2C:
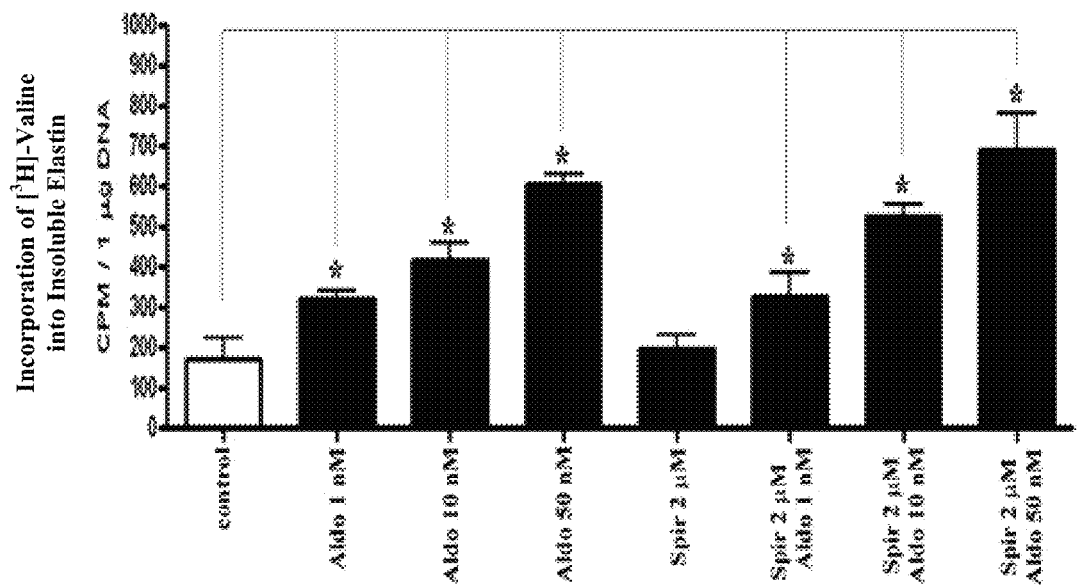
Figure 2D:
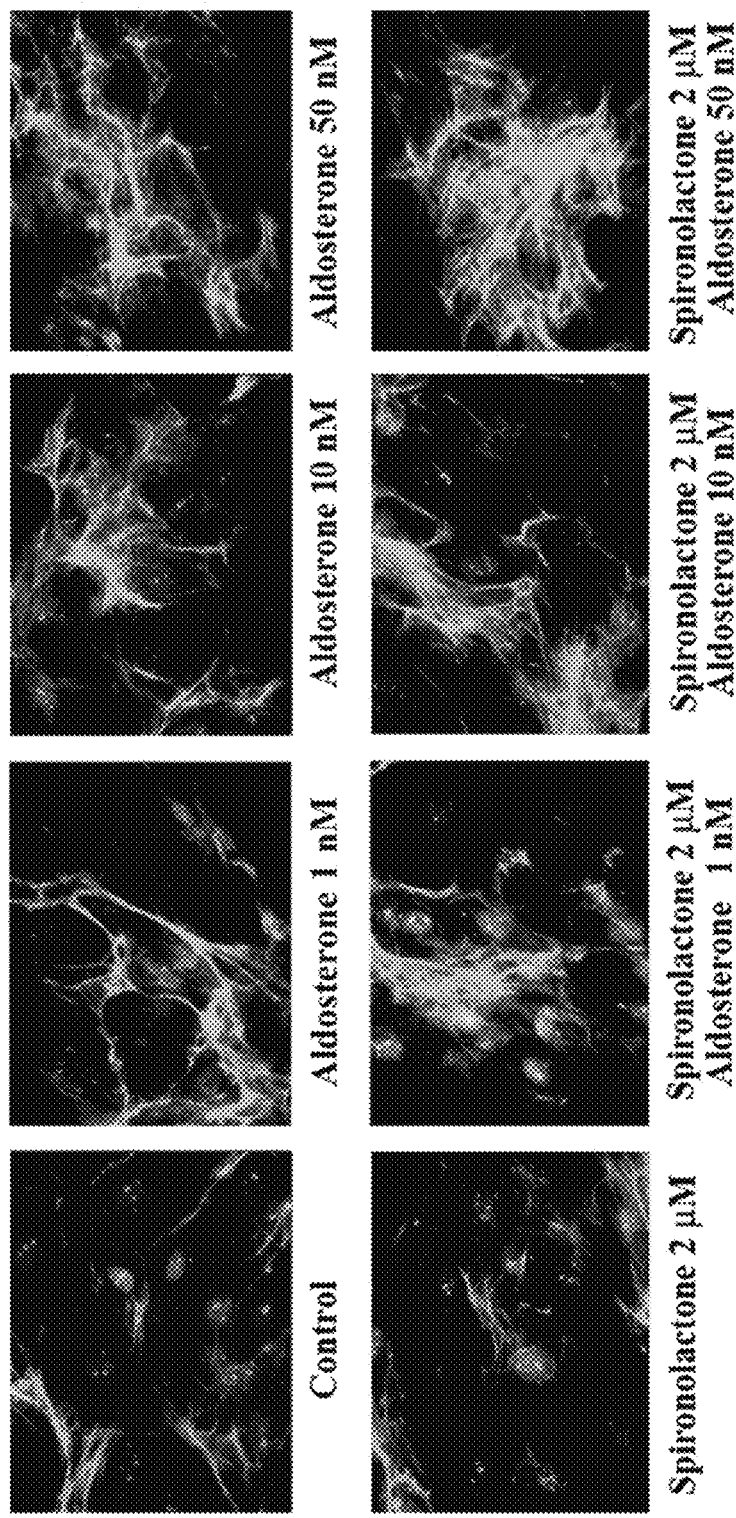

Aldosterone Up-Regulates Elastin Gene Expression and the Net Deposition of Elastic Fibers in an MR-Independent Manner in Cultures of Cardiac Fibroblasts Isolated from Fetal and Adult Human Hearts Analysis of parallel cultures revealed that aldosterone also up-regulated the effective expression of the elastin gene, as detected by heightened elastin mRNA levels, in a dose-dependent manner (FIG. 2A). This was translated to a proportional increase in the net levels of newly synthesized metabolically labeled intracellular tropoelastin and in the net deposition of metabolically labeled insoluble elastin, the major component of elastic fibers (FIG. 2, B-D). It is also noted that raising aldosterone far above "physiological" levels (100 nmol/L and 1 μmol/L) did not produce any cytotoxic effects but led to a further increase in elastin production.

Surprisingly, pretreatment of cardiac fibroblasts with spironolactone, which eliminated any aldosterone-induced increase in collagen type I production, failed to prevent an aldosterone-induced increase in elastin mRNA expression and in the net content of metabolically labeled intracellular tropoelastin and insoluble elastin (FIG. 2). These observations suggest that aldosterone probably induces elastogenesis through an MR-independent process. To exclude the possibility that the increase in elastin production following aldosterone treatment may be mediated through GR activation, cardiac fibroblasts cultures were also preincubated with the GR antagonist RU 486 (1 μmol/L) in the presence of 1 to 50 nmol/L aldosterone. Results demonstrated that RU 486 had no effect on the aldosterone-induced increase in elastin mRNA levels (FIG. 2A).

Figure 3:
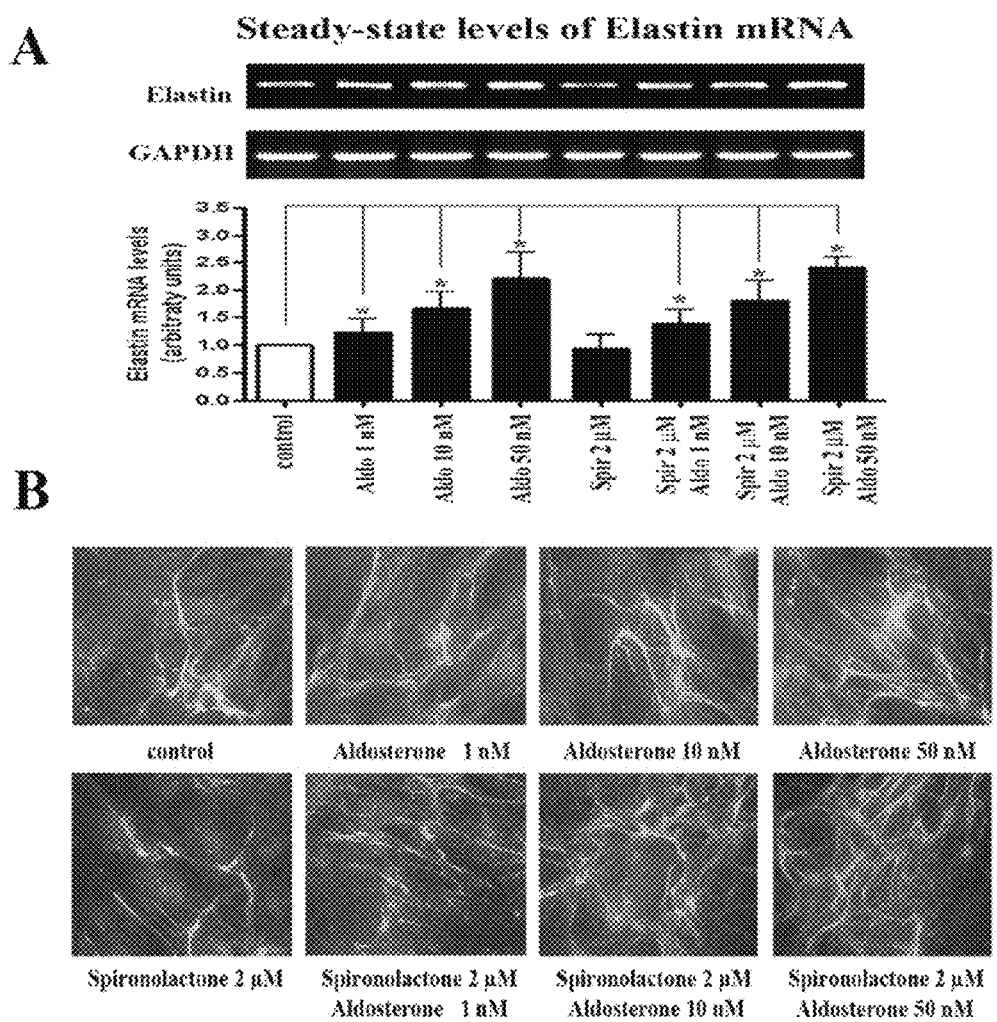
FIG. 3. The effect of aldosterone and the MR antagonist spironolactone on elastin mRNA levels and elastic fiber deposition in confluent cultures of adult cardiac fibroblasts. A: One-step RT-PCR analysis assessing elastin mRNA transcripts in cultures treated for 24 hours in the presence or absence of 1 to 50 nmol/L aldosterone, with or without spironolactone, and normalized to the corresponding levels of GAPDH mRNA. The results indicate that 1 to 50 nmol/L aldosterone treatment dose-dependently increased elastin mRNA transcript levels compared with untreated control values (*P<0.05). Pretreatment of cells for 1 hour with spironolactone before aldosterone treatment had no effect on the aldosterone-induced increase in elastin mRNA transcript levels. B: Representative photomicrographs of confluent cultures immunostained with anti-elastin antibody demonstrate that 1 to 50 nmol/L aldosterone treatment for 72 hours significantly increased the number of immunodetectable elastic fibers compared with untreated controls, and that spironolactone pretreatment did not affect aldosterone-induced increase in elastic fiber deposition.

To eliminate the possibility that the observed effects might be restricted to fetal cardiac fibroblasts, stromal fibroblasts isolated from adult human hearts to test the influence of aldosterone on their elastogenic abilities. Results showed that the elastogenic response of adult cardiac fibroblasts to aldosterone and spironolactone was similar to that of their fetal counterparts (FIG. 3).

Example 3

Aldosterone-Induced Increase in Elastin Deposition Involves Activation of the IGF-I Receptor To explore further the mechanism by which aldosterone induces elastogenesis in an MR-independent manner, membrane-impermeable BSA-conjugated aldosterone was used to determine whether aldosterone would induce elastogenesis by the stimulation of cell surface receptors without internalization. Treatment of cardiac fibroblast cultures with 1, 10, or 50 nmol/L aldosterone conjugated to BSA produced the same effect on elastin mRNA levels and consequent elastin production as treatment with equimolar free aldosterone (FIG. 4).

To identify the putative cell surface-residing component involved in the MR-independent action of aldosterone, the activation of selected cell surface receptors was blocked to test whether this might eliminate aldosterone-induced elastogenesis. Results showed that pretreatment of cultured cardiac fibroblasts with inhibitors of selected growth factor receptors EGF (AG 1478), transforming growth factor β (SB 431542), and platelet-derived growth factor BB (AG 1295), did not affect the aldosterone-induced increase in elastin production. In addition, treatment with G protein inhibitor, pertussis toxin, or staurosporine (to inhibit protein kinase C activity) did not abrogate the aldosterone-induced increase in elastin production (data not shown).

On the other hand, blocking the IGF-IR with a specific inhibitor, AG 1024, eliminated the stimulatory effect of aldosterone on elastin mRNA expression and insoluble elastin production (FIGS. 5 A, C, and E). Because AG 1024 specifically inhibits ligand-stimulated autophosphorylation of the IGF-IR but not of the insulin receptor, it was proposed that aldosterone may engage IGF-IR signaling to stimulate elastogenesis. In support, blocking the IGF-IR with 1 μg/ml IGF-IR neutralizing antibody before aldosterone treatment eliminated the elastogenic effect (FIGS. 5, A, C, and E). Furthermore, results showed that treating cardiac fibroblasts with 100 ng/ml IGF-I led to an approximately threefold increase in elastin mRNA levels and in the net production of insoluble elastin. Results also showed that this increase could be prevented by pretreating the fibroblasts with 5 μmol/L AG 1024 or with 1 μg/ml IGF-IR neutralizing antibody (FIGS. 5, B and D).

Figure 6C:
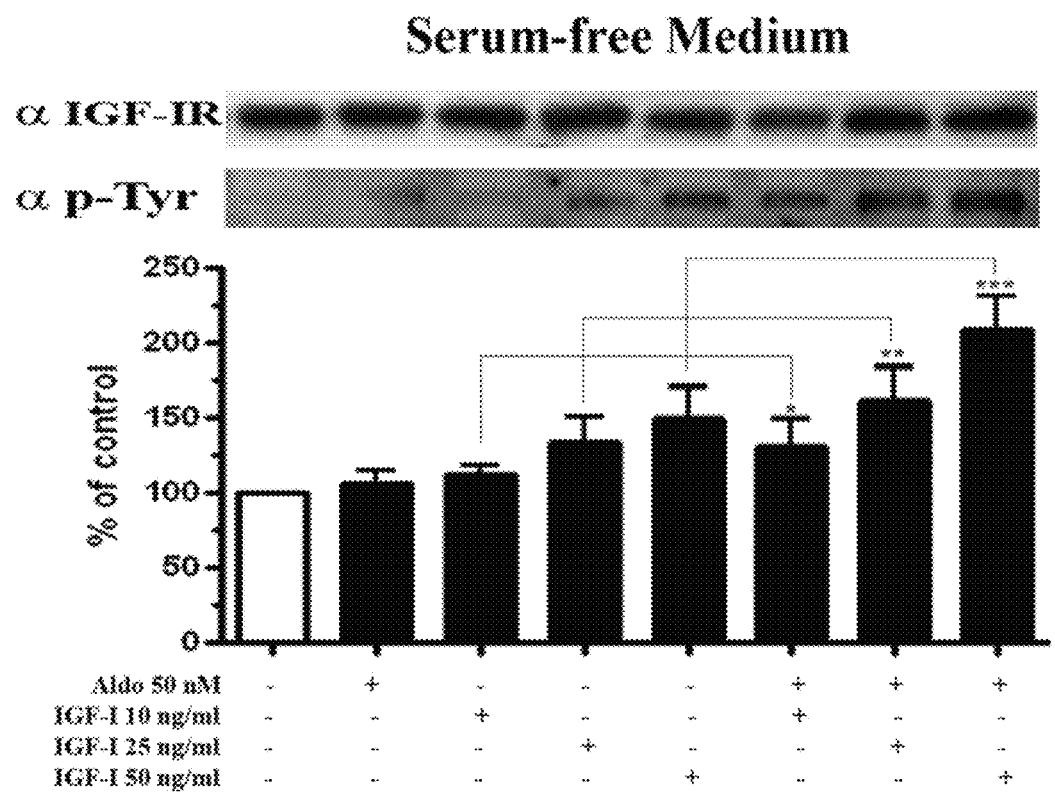

To determine whether tyrosine phosphorylation of the IGF-IR is affected by aldosterone treatment, we performed IGF-IR immunoprecipitation from cultures incubated in the presence and absence of 50 nmol/L aldosterone for 10, 15, 30, and 60 minutes. Results showed that a 10-minute exposure to 50 nmol/L aldosterone led to a transient increase in tyrosine phosphorylation of the IGF-IR above basal level. Exposure for 10 minutes to 100 ng/ml IGF-I produced a very similar effect (FIGS. 6, A and B). However, whereas IGF-I induced phosphorylation of its IGF-IR, both in the presence and in the absence of fetal bovine serum, aldosterone induced a similar effect only in the presence of serum. These results suggest that aldosterone may facilitate but not induce IGF-IR-dependent signaling. In further experiments, cultures treated with 50 nmol/L aldosterone and 10, 25, or 50 ng/ml IGF-I showed higher levels of IGF-IR tyrosine phosphorylation than their respective counterparts treated with the same doses of IGF-I alone (FIG. 6C).

Because membrane-impermeable BSA-conjugated aldosterone produced the same effect on elastin mRNA levels and consequent elastin production as treatment with equimolar free aldosterone (FIG. 4), it is possible that aldosterone may exert its MR-independent effect by interaction with certain cell surface-residing moieties. For example, without being bound by theory, aldosterone may exert its effect through an angiotensin II type I receptor which, in turn, could transactivate the IGF-IR, or it may involve cytosolic tyrosine kinases of the c-Src family, which have been shown to transactivate EGFR in response to aldosterone treatment.

Example 4

In Vivo Infarct Studies

Data from a parallel study that was conducted on a rat myocardial infarction model indicated that animals treated with eplerenone during the postinfarction period produced scars with abundant elastic fibers that replaced the mostly collagenous scars seen in vehicle-treated animals.

Example 5

Pulmonary Studies

The effect of elastin production on pulmonary fibroblasts is tested by adding aldosterone to pulmonary fibroblasts with or without spironolactone. These data demonstrate the feasibility of using such an approach to treat pulmonary dysfunctions related to scarring such as for example, pulmonary fibrosis and emphysema. In some experiments, spironolactone is administered in vivo as a tablet and aldosterone is inhaled.

Example 6

Keloid Therapy

The compositions disclosed herein are used to treat keloids. Specifically, the keloid growth is treated with corticosteroids to decrease collagen production. Subsequently, collagenase is administered at a site of scarring and then the aldosterone and spironolactone is administered. In some experiments, aldosterone is administered locally as a cream/injection and spironolactone is administered as a tablet.

Example 7

Aldosterone Stimulates Elastogenesis in Cardiac Fibroblasts Via MR-independent Action Involving the Consecutive Activation of Gα13, c-Src, the IGF-I Receptor, and PI3 Kinase/Akt Aldosterone, which stimulates collagen production through the mineralocorticoid receptor (MR)-dependent pathway, also induces elastogenesis via a parallel MR-independent mechanism involving insulin-like growth factor-I receptor (IGF-IR) signaling. Present invention demonstrates that siRNA-driven elimination of MR in cardiac fibroblasts does not inhibit aldosterone-induced IGF-IR phosphorylation and subsequent increase in elastin production. These results exclude the involvement of the MR in aldosterone-induced increases in elastin production. Results of further experiments aimed at identifying the upstream signaling component(s) that are activated by aldosterone also eliminate the putative involvement of pertussis toxin-sensitive Gαi proteins, which is responsible for some MR-independent effects of aldosterone. We found that siRNA-dependent elimination of another heterotrimeric G protein, Gα13, eliminates aldosterone-induced elastogenesis. We further demonstrate that aldosterone first engages Gα13 and then promotes its transient interaction with c-Src, which constitutes a prerequisite step for aldosterone-dependent activation of the IGF-IR and propagation of consecutive downstream elastogenic signaling involving PI3 kinase/Akt.

In summary, the data we present reveal new details of an MR-independent cellular signaling pathway through which aldosterone stimulates elastogenesis in human cardiac fibroblasts.

Aldosterone is a major component of the renin-angiotensin-aldosterone system, which plays an important role in the regulation of electrolyte and fluid balance. The majority of aldosterone-induced effects occur after it binds to the intracellular MR. The activated aldosterone-MR complex translocates to the nucleus, where it modulates the transcription and translation of "aldosterone-induced" proteins involved in blood pressure homeostasis.

Aldosterone has also been implicated in the stimulation of collagen synthesis and myocardial fibrosis through a process that is independent of its effect on blood pressure. Two clinical studies, the Randomized Aldactone Evaluation Study (RALES) and the Eplerenone Post-acute Myocardial Infarction Heart failure Efficacy and Survival Study (EPHESUS), demonstrated that low doses of MR antagonists lead to a dramatic reduction in the mortality rate of patients who suffered acute myocardial infarctions.

Aldosterone can induce numerous effects in a wide range of non-epithelial tissues, including heart, and that acts through membrane receptors other than the traditional MR (alternative receptors) in epithelial and nonepithelial tissue in a non-genomic manner.

Some of the non-genomic effects of aldosterone also require the presence of MR or a closely related protein. Non-genomic aldosterone effects still occur in cell lines lacking the classical MR and in yeast devoid of MR or in normal cells treated with MR antagonists. Other receptor(s), distinct from the classic MR, interact with aldosterone and trigger the non-genomic effects of this hormone. Although full structural characterization of this putative receptor (or receptors) has not been completed, it is understood that some MR-independent effects of aldosterone occur after activation of the pertussis toxin-sensitive heterotrimeric G proteins.

Results of our previous studies have revealed a novel mechanism in which aldosterone and its antagonists modulate the production of elastin, an important ECM component that provides resilience to many tissues, including stroma of the heart. We discovered that aldosterone can stimulate elastogenesis in cultures of human cardiac fibroblasts via an MR-independent mechanism involving IGF-IR activation. We have therefore uncovered another level of complexity in which aldosterone in conjunction with MR antagonists may modulate the remodeling of the injured heart.

In the present study, we provide compelling evidence demonstrating that cultured cardiac fibroblasts, in which the production of MR has been inhibited by siRNA, still exhibit the aldosterone-induced increase in elastin production. We also present the first evidence that this MR-independent elastogenic effect of aldosterone can be triggered by a signaling pathway that involves initial activation of the heterotrimeric G protein Gα13 and consecutive activation of c-Src, IGF-IR, and PI3 kinase/Akt signaling.

Materials—All chemical-grade reagents, aldosterone, proteinase inhibitors, agarose-linked protein A, pertussis toxin, recombinant human insulin-like growth factor-I (IGF-I), PD 98059, PD123319, aluminum chloride (AlCl3) and sodium fluoride (NaF), as well as secondary antibodies fluorescein-conjugated goat anti-rabbit, fluorescein-conjugated goat anti-mouse, and fluorescein-conjugated rabbit anti-goat were obtained from Sigma (St. Louis, Mo.). Wortmannin, PP2, SP600125, and Y-27632 were purchased from Calbiochem (San Diego, Calif.). Losartan was purchased from Cayman Chemicals Co. (Ann Arbor, Mich.). A cell-permeable Rho inhibitor (exoenzyme C3 transferase, CT04) was purchased from Cytoskeleton, Inc. (Denver, Colo.). Iscove's modified Dulbecco's Medium (IMDM), fetal bovine serum, 0.2% trypsine-0.02% EDTA, and other cell culture products were acquired from GIBCO Life Technologies (Burlington, ON). Polyclonal antibody to tropoelastin was purchased from Elastin Products (Owensville, Mich.). Polyclonal antibody to collagen type I was purchased from Chemicon (Temecula, Calif.). Polyclonal antibodies against phosphorylated c-Src (Tyr-416), total c-Src, phosphorylated Akt (Ser437), total Akt, and monoclonal antibody against β-actin and GAPDH were purchased from Cell Signaling Technology, Inc. (Danvers, Mass.). Monoclonal antibody against phosphotyrosine (PY99), polyclonal antibody against IGF-IR-β and MR, rabbit and goat polyclonal antibodies against Gα13, rabbit polyclonal antibody against Gα12, normal rabbit or goat agarose conjugated-IgGs, and rabbit polyclonal antibody and mouse monoclonal antibody against c-Src as well as human whole cell lysates were obtained from Santa Cruz Biotechnology (Santa Cruz, Calif.). Mouse monoclonal antibody against MR was purchased from ABR Affinity BioReagents (Golden, Colo.). Species- and type-specific secondary antibodies conjugated to horseradish peroxidase, an enhanced chemiluminescence kit, and the radiolabeled reagent [3H]-valine were purchased from Amersham Biosciences Canada Ltd. (Oakville, ON). Precast 4-12% tris-glycine gel was purchased from Invitrogen Canada Inc. (Burlington, ON). A DNeasy Tissue system for DNA assay, RNeasy Mini Kit for isolating total RNA, and One-Step RT-PCR Kit were purchased from Qiagen (Mississauga, ON). Two different pre-designed G$\alpha$13 siRNA oligonucleotide duplexes were purchased from Ambion, Inc. (Austin, Tex.), and a custom designed G$\alpha$13 siRNA oligonucleotide duplex, as well as predesigned ON-TARGETplus SMART pool MR siRNA, was purchased from Dharmacon (Lafayette, Colo.). A DeliverX plus siRNA transfection reagent kit, including GAPDH specific siRNA and non-silencing (scrambled) siRNA oligonucleotide duplexes, was purchased from Panomics, Inc. (Fremont, Calif.). BSA-conjugated aldosterone (aldo-BSA) was purchased from Fitzgerald Industries Intl (Concord, Mass.). As specified by the manufacturer, 25 aldosterone molecules are covalently linked to each BSA molecule through a carboxymethyl oxyme residue on the C3 of the hormone, forming a stable conjugate.

Cultures of human cardiac fibroblasts—We used cardiac fibroblasts isolated from human fetal hearts (which are responsible for the production of cardiac ECM) to make our studies clinically relevant. Human fetal cardiac fibroblasts of 20-22 weeks gestation, a generous gift from Dr. John Coles, were prepared in accordance with an institutional review board-approved protocol. Confluent cultures were passaged by trypsinization and maintained in IMDM supplemented with 1% antibiotics/antimycotics and 10% fetal bovine serum. Passage 1-3 cells were used in all experiments. The purity of these cultures at passage 1 was 95%. Cardiac fibroblasts were determined by positive staining for vimentin and negative for von Willebrand factor and $\alpha$-smooth muscle cell actin, as previously described.

In experiments aimed at assessing ECM production, fibroblasts were initially plated (100,000 cells/dish) and maintained in a normal medium until confluency, the point at which they produce abundant ECM. Confluent cultures were then treated for 72 hours with or without 50 nM of aldosterone.

In separate experiments, we tested the influence of an equimolar concentration of aldosterone that was coupled to bovine serum albumin (BSA), which prevents it from penetrating into the cell interior. The G-protein inhibitor pertussis toxin, MAPK kinase inhibitor PD98059, c-Jun N-terminal kinases (JNK) inhibitor SP600125, PI3 kinase inhibitor wortmannin, c-Src tyrosine kinase inhibitor PP2, and Rho-associated kinase (ROCK) inhibitor Y-27632, as well as the AT1 receptor antagonist losartan and the AT2 receptor antagonist PD123319, were added 1 hour prior to aldosterone treatment. Cell permeable Rho inhibitor (CTO4) was added 2 hours prior to aldosterone treatment, as specified by the manufacturer. Cells were also treated for 3 hours with aluminum fluoride solution (AlCl3 and NaF) prepared immediately before use. All control cell cultures received an equal amount of the solvent vehicle.

Immunostaining—At the end of the 72-hour incubation period with the indicated treatment, confluent cultures were fixed in cold 100% methanol at −20° C. (for elastin and MR staining) or in 4% paraformaldehyde at room temperature (for collagen staining) for 30 minutes and blocked with 1% normal goat serum for 1 hour at room temperature. The cultures were then incubated for 1 hour either with 10 µg/ml of polyclonal antibody to tropoelastin, 10 µg/ml of monoclonal antibody to MR, or with 10 µg/ml of polyclonal antibody to collagen type I. All cultures were then incubated for an additional hour either with fluorescein-conjugated goat anti-rabbit, fluorescein-conjugated goat anti-mouse, or with fluorescein-conjugated rabbit anti-goat secondary antibodies to detect elastin, MR, and collagen type I staining respectively. Nuclei were counterstained with propidium iodide. Secondary antibody alone was used as a control. All of the cultures were then mounted in elvanol and examined with a Nikon Eclipse E1000 microscope attached to a cooled CCD camera (QImaging, Retiga EX) and a computer-generated video analysis system (Image-Pro Plus software, Media Cybernetics, Silver Springs, Md.).

Quantitative assay of insoluble elastin—Fetal human cardiac fibroblasts were grown to confluency in 35-mm culture dishes (100,000 cells/dish) in quadruplicate. Then 2 µCi of [3H]-valine/ml of fresh media were added to each dish and treated as specified. Following a 72-hour incubation, the cells were extensively washed with PBS, and the cells including deposited insoluble ECM were scraped and boiled in 500 µl of 0.1 N NaOH for 30 minutes to solubilize all matrix components except elastin. The resulting pellets containing the insoluble elastin were then solubilized by boiling in 200 µl of 5.7 N HCl for 1 hour, and the aliquots were mixed in scintillation fluid and counted. Aliquots taken from each culture were also used for DNA determination using the DNeasy Tissue System from Qiagen. Final results reflecting the amounts of metabolically labeled insoluble elastin in the individual cultures were normalized according to their DNA content and expressed as CPM/1 µg DNA.

One-Step RT-PCR analysis—Confluent fetal human cardiac fibroblast cultures were treated with or without the specified treatment for 24 hours, unless otherwise indicated. Total RNA was extracted using the RNeasy Mini Kit according to the manufacturer's instructions, 1 µg of total RNA was added to each one-step RT-PCR kit, and reactions were set up according to the manufacturer's instructions in a total volume of 25 µl. The reverse transcription step was performed for elastin and GAPDH reactions at 50° C. for 30 minutes, followed by 15 minutes at 95° C. The elastin PCR reaction (sense primer: 5'-GGTGCGGTGGTTCCTCAGCCTGG-3; antisense primer: 5'-GGGCCTTGAGATAC-CCCAGTG-3; designed to produce a 255 bp product) was performed under the following conditions: 25 cycles at 94° C. denaturation for 20 seconds, 63° C. annealing for 20 seconds, 72° C. extension for 1 minute, and 1 cycle at 72° C. final extension for 10 minutes. The G$\alpha$13 PCR reaction (sense primer: 5'-CGT-GATCAAAGGTAT-GAGGG-3; antisense primer: 5'-CA-GATTCA-CCCAGTTGAAATT-3; designed to produce a 249 bp product) was performed under the following conditions: 25 cycles at 94° C. denaturation for 30 seconds, 60° C. annealing for 30 seconds, 72° C. extension for 1 minute, and 1 cycle at 72° C. final extension for 10 minutes. The collagen type I (pro-$\alpha$1(I) chain) PCR reaction (sense primer: 5'-CCCACCAATCACCTGCGTA-CAGA-3', antisense primer: 5'-TTCTTGGTCGG-TGGGTGACTCTGA-3') was performed under the following conditions: 20 cycles at 94° C. denaturation for 30 seconds, 58° C. annealing for 30 seconds, 72° C. extension for 10 minutes, and 1 cycle at 72° C. final extension for 10 minutes. The GAPDH PCR reaction (sense primer: 5'-TCCACCACCCTGTTGCTGTAG-3; antisense primer: 5'-GACCACAGTCCATGC-CATC ACT-3; designed to produce a 450 bp product) was performed under the following conditions: 21 cycles at 94° C. denaturation for 20 seconds, 58° C. annealing for 30 seconds, 72° C. extension for 1 minute, and 1 cycle at 72° C. final extension for 10 minutes. 5 µl samples of the elastin, Gα13, collagen type I, and GAPDH PCR products from each reaction were run on a 2% agarose gel and post-stained with ethidium bromide. The amount of elastin, Gα13, and collagen type I mRNA was standardized relative to the amount of GAPDH mRNA.

Western blotting—Confluent fetal human cardiac fibroblast cultures were exposed with or without the treatment specified for the indicated time points. At the end of each experiment cells were lysed using an RIPA buffer (50 mM Tris.HCl, pH 7.4; 150 mM NaCl; 1 mM EDTA; 10 mM NaF; 1% Triton X-100; 0.1% SDS; 1% Na deoxycholate) containing a cocktail of antiproteases (20 µg/ml leupeptin, 10 µg/ml aprotinin, 0.1 mM PMSF, 1 mM DTT) and antiphosphates (200 M orthovanadate, 2 µg/ml pepstatin). Then 40-60 µg of protein extract was resuspended in sample buffer (0.5 M Tris.HCl, pH 6.8; 10% SDS; 10% glycerol; 4% 2-β-mercaptoethanol; and 0.05% bromophenol blue), and the mixture was boiled for 5 minutes. Protein lysates were resolved by precast SDS-PAGE gel (4-12% gradient), transferred to nitrocellulose membranes, blocked for an hour, and then immunoblotted with polyclonal anti-MR antibody, anti-phospho-c-Src (Tyr416) antibody, anti-phospho-Akt (Ser473) antibody, anti-Gα13 (goat) antibody, anti-SCAP2 antibody, or with buffer (TBS-T) at 4° C. overnight. All blots were then incubated with the appropriate HRP-conjugated secondary antibodies for an hour and examined using the enhanced chemiluminescence detection system. Blots were stripped and reprobed using specified antibodies. For all western blot experiments human whole cell lysates were also electrophoresed and immunoblotted with the mentioned antibodies that served as a positive control and accordingly produced the appropriate molecular weight band. The degree of expression or phosphorylation of immunodetected signaling molecules was measured by densitometry.

Immunoprecipitation—To evaluate the level of IGF-IR-β phosphorylation, confluent fetal human cardiac fibroblast cultures were incubated for the indicated time in the presence or absence of 50 nM aldosterone, or for 10 minutes with 100 ng/ml of IGF-I. For co-immunoprecipitation experiments, confluent cultures were incubated with the treatment. At the end of each experiment the cells were lysed as specified above, and 300 µg of protein extract were then precleared for 1 hour with normal rabbit agarose conjugated-IgG at 4° C. and incubated with rabbit polyclonal antibodies against IGF-IR-β, c-Src, or with Gα13 for 1 hour at 4° C., followed by the addition of 4% protein A-beaded agarose and left overnight. The resulting protein-antibody conjugate was centrifuged at 4° C. and washed four times with PBS. The final pellet was resuspended in sample buffer, and the proteins were resolved. Following immunoprecipitation of IGF-IR-β, the membrane was immunoblotted using monoclonal anti-p-Tyr antibody, stripped, and reprobed using anti-IGF-IR-β. Following immunoprecipitation of c-Src, the membranes were immunoblotted using polyclonal goat antibodies against anti-Gα13, while those immunoprecipitated with anti-Gα13 were developed with monoclonal anti-c-Src antibody. Blots were stripped and re-probed for equal loading.

For all immunoprecipitation experiments, rabbit IgG was also immunoprecipitated and used as a negative control and accordingly did not produce a band. The degree of expression or phosphorylation of immunodetected signaling molecules was measured by densitometry.

Silencing MR and Gα13 expression using siRNA-specific oligonucleotides MR- and Gα13-specific siRNA oligonucleotides—ON-TARGET plus SMART pool MR siRNA (gene ID 4306) containing a mixture of 4 SMART-selection predesigned siRNAs exclusively targeting MR (MR siRNA) was purchased from Dharmacon (Lafayette, Colo.). Two different Silencer® predesigned siRNA duplexes against human Gα13 (standard purity, siRNA ID #119735 and 119733) were obtained from (Ambion). The custom designed oligonucleotide duplex (Dharmacon) was synthesized to correspond to target sequences on the full-length human Gα13 protein. The custom designed oligonucleotide target sequence was as follows: 5'-GAA GAU CGA CUG ACC CAA UC-3', which was previously shown to completely eliminate Gα13 in HeLa cells. A non-silencing control and GAPDH siRNA duplex sequences (Panomics) were used as controls for the transfections.

Transfection of MR and Gα13 siRNA oligonucleotides—Cardiac fibroblasts were seeded in 6-well plates, maintained in IMDM medium supplemented with 10% fetal bovine serum, penicillin (100 U/ml), and streptomycin (100 µg/ml). 80-90% confluent cardiac fibroblast cultures were washed in PBS, and 30 nM of Gα13, GAPDH, or non-silencing siRNA or 90 nM of MR or non-silencing siRNA were transfected into cells using DeliverX plus siRNA transfection reagent (Panomics), according to the manufacturer's instructions. MR production was monitored by Western blotting, while Gα13 expression was monitored by one-step RT-PCR and Western blotting post-transfection. The Gα13 siRNA 1 oligonucleotide (Ambion) provided the greatest knockdown of Gα13 and was used in all siRNA experiments to silence Gα13 expression.

Data analysis—In all biochemical studies, quadruplicate samples in each experimental group were assayed in three separate experiments. Mean and standard deviations (SD) were calculated for each experimental group, and statistical analyses were carried out by ANOVA. A P value of less than 0.05 was considered significant.

Results—The absence of MR does not prevent an aldosterone-induced increase in IGF-IR phosphorylation and subsequent elastin production in cultures of cardiac fibroblasts Treatment with 1-50 nM of aldosterone increases elastin mRNA levels, tropoelastin synthesis, and elastic fiber deposition in a dose-dependent manner. Strikingly, neither spironolactone (an MR antagonist) nor RU 486 (a glucocorticoid receptor antagonist) eliminated aldosterone-induced increases in elastin production, which were induced after aldosterone-dependent phosphorylation of IGF-IR.

Figure 7A:
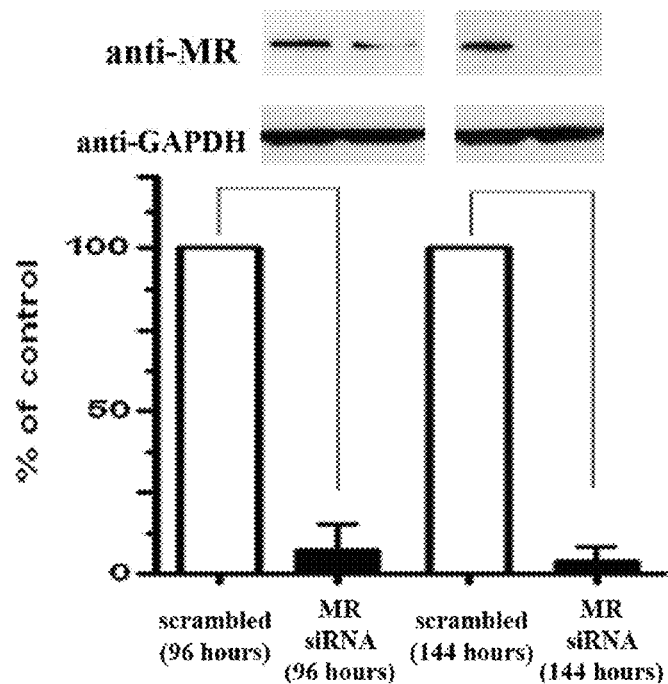
FIG. 7. Eliminating the production of MR with siRNA specific oligonucleotides in cultures of human cardiac fibroblast does not affect aldosterone-induced increases in elastin production. (A) Representative Western blots of cellular lysates from cultures that were transfected for either 96 hours or for 144 hours with scrambled and MR siRNA specific oligonucleotides (A) and densitometric evaluation of results obtained from three individual experiments indicate that levels of immuno-detected MR protein levels were significantly decreased, both 96 hours (P<0.05) and 144 hours after transfection (*P<0.05), as compared to control levels in cells transfected with scrambled nucleotides. (B) Immunohistochemistry with anti-MR antibody also confirmed that production of MR was completely attenuated in cultures that were transfected with MR siRNA. (C—left panel) Results of a quantitative assay of newly deposited insoluble elastin metabolically labeled with [$^3$H]-valine in cultures that were initially transfected for 72 hours with scrambled or Gα13 siRNA and then transfected again for an additional 72 hours and kept in the presence or absence of 50 nM of aldosterone. (C—right panel) Representative photomicrographs of confluent cultures immunostained with anti-elastin antibody also confirmed these results. Initial magnification 600×. (D) The 10-minutes exposure to 50 nM of aldosterone, which produced a transient increase in tyrosine phosphorylation of the IGF-IR in control cultures, produced a similar increase in cultures transfected for 96 hours with Gα13 siRNA specific oligonucleotides. (E) The 10-minutes exposure to 50 nM of membrane-impermeable, BSA-conjugated aldosterone produced the same effect on IGF-IR phosphorylation as treatment with identical dose of free aldosterone. Cell lysates were immunoprecipitated with an IGF-IR antibody, and then analyzed by Western blots with an anti-phospho-tyrosine (anti-phospho-tyr) antibody or anti-IGF-IR antibody. Graphs depict the mean±SD values (phospho-IGF-1R/total-IGF-1R) from three individual experiments,*(P<0.05).
Figure 7B:
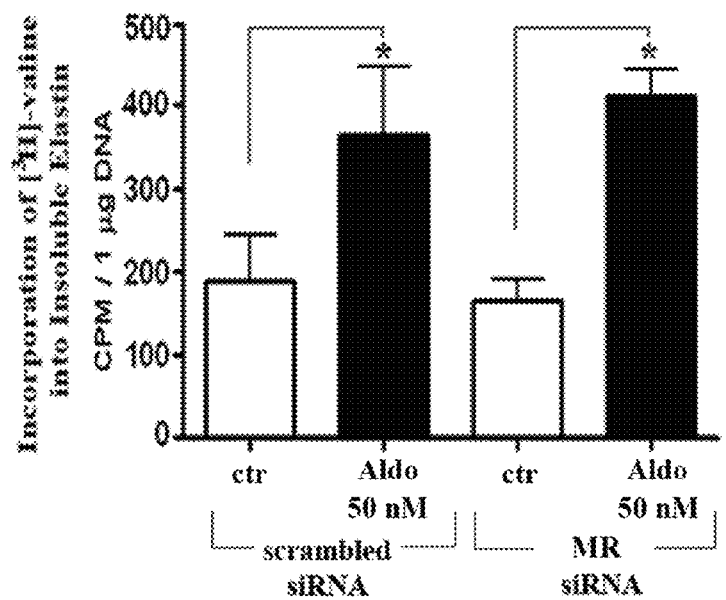
Figure 7C:
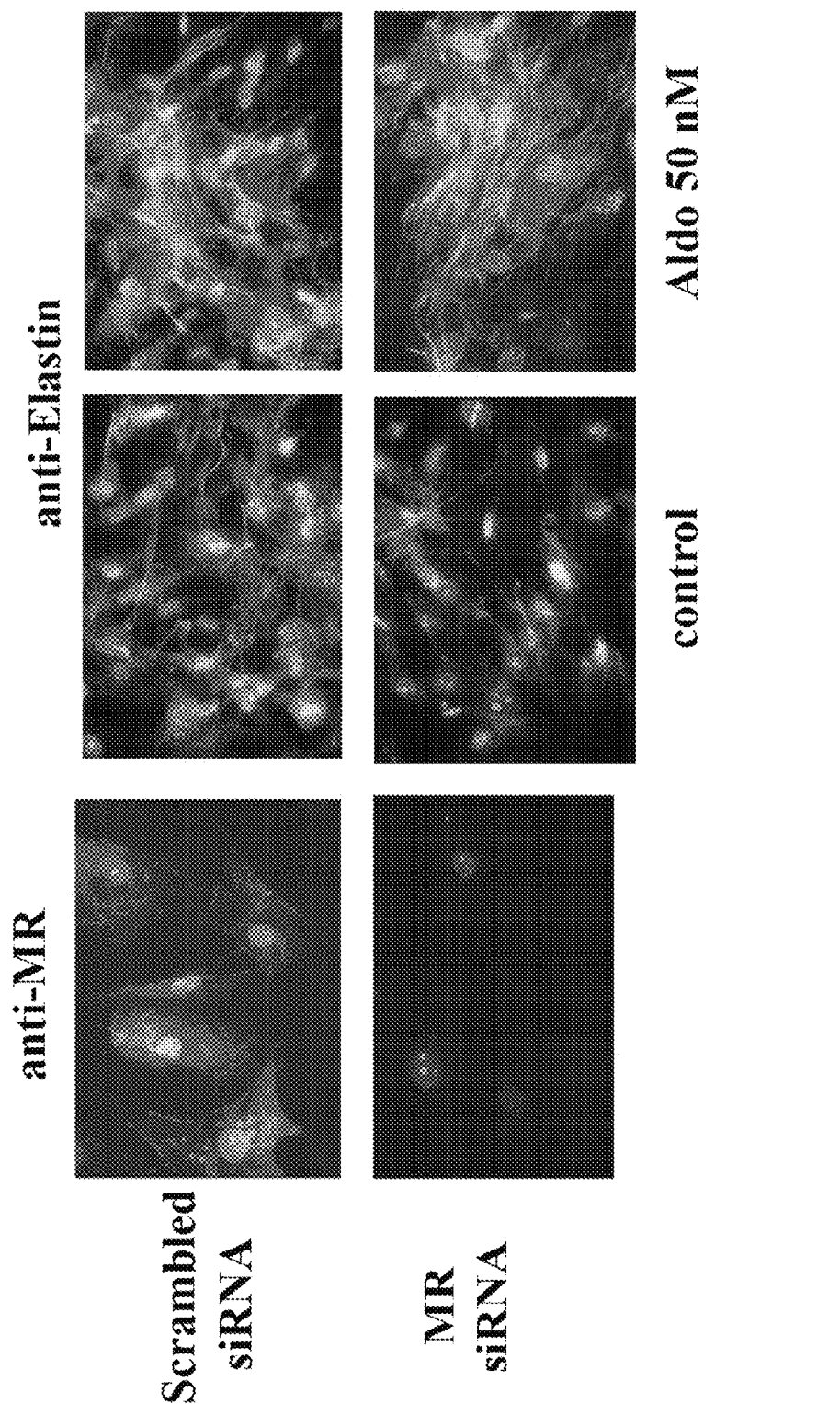
Figure 7D:
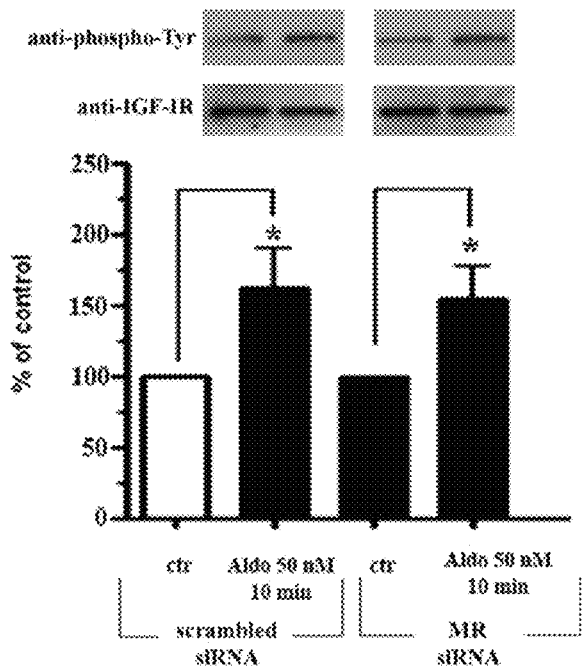
Figure 7E:
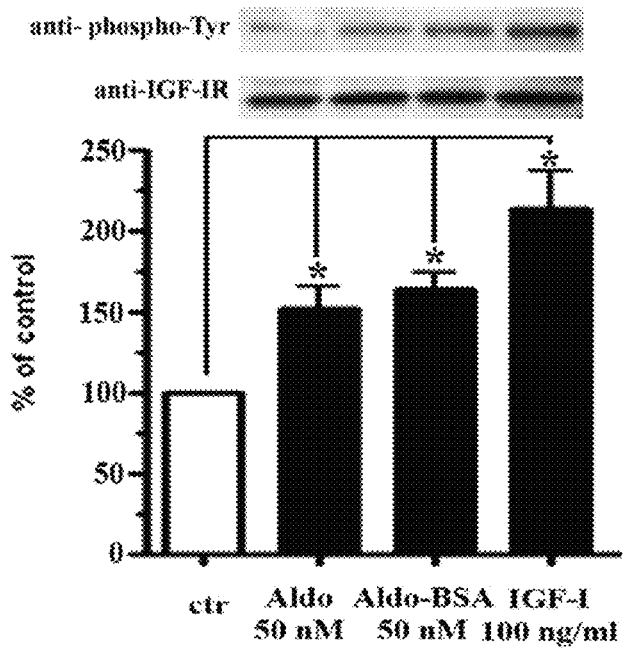

The present study produces a detailed characterization of the signaling pathway through which aldosterone upregulates elastin production. We first used MR-specific siRNA oligonucleotides to eliminate the production of MR in cardiac fibroblast cultures in order to exclude the conventional involvement of MR in aldosterone-induced elastogenesis. The densitometric evaluation of results obtained from three individual experiments (FIG. 7 A) indicated that levels of immuno-detected MR protein decreased to approximately 11% of the scrambled control levels 96 hours after transfection (P<0.05) and to approximately 6% of scrambled control levels 144 hours after transfection (P<0.05). Immunohistochemistry with anti-MR antibody also confirmed that production of MR was completely attenuated in cultures that were transfected with MR siRNA. Importantly, results of the consecutive experiments demonstrated that this effective siRNA-dependent inhibition of MR synthesis in cultures of cardiac fibroblasts (FIGS. 7 A and B,) did not diminish their elastogenic response to 50 nM of aldosterone (FIG. 7 C). Furthermore, we also showed that a 10-minute exposure to 50 nM of aldosterone, which produced a transient increase in tyrosine phosphorylation of the IGF-IR in control cultures, produced a similar increase in cultures treated with MR siRNA (FIG. 7 D). Then we utilized BSA-conjugated aldosterone to determine whether this membrane-impermeable form of aldosterone would trigger IGF-IR phosphorylation by direct stimulation of a cell surface-residing component (or components). Indeed, treatment for 10 minutes with 50 nM of BSA-conjugated aldosterone produced the same effect on IGF-IR phosphorylation as treatment with equimolar free aldosterone (FIG. 7E).

The search for the cell-membrane component(s) involved in aldosterone-induced elastogenesis. The results described above suggested that MR-independent activation of the IGF-IR leading to increased elastin production by aldosterone does not require the entry of this hormone into the cell interior. We therefore concluded that such an effect is triggered through the direct interaction of aldosterone with certain cell membrane-residing component(s).

MR-independent effects of aldosterone may be induced through the modulation of angiotensin II-dependent signaling, therefore, we first examined that aldosterone-induced elastogenesis might involve the cross-activation of angiotensin II receptor(s). Our results demonstrated that the addition of angiotensin II type I (losartan) and angiotensin II type 2 (PD 123319) receptor antagonists to cultures of cardiac fibroblasts did not abrogate their elastogenic response to aldosterone. Thus, the possibility that angiotensin II receptors were involved was eliminated.

Figure 8:
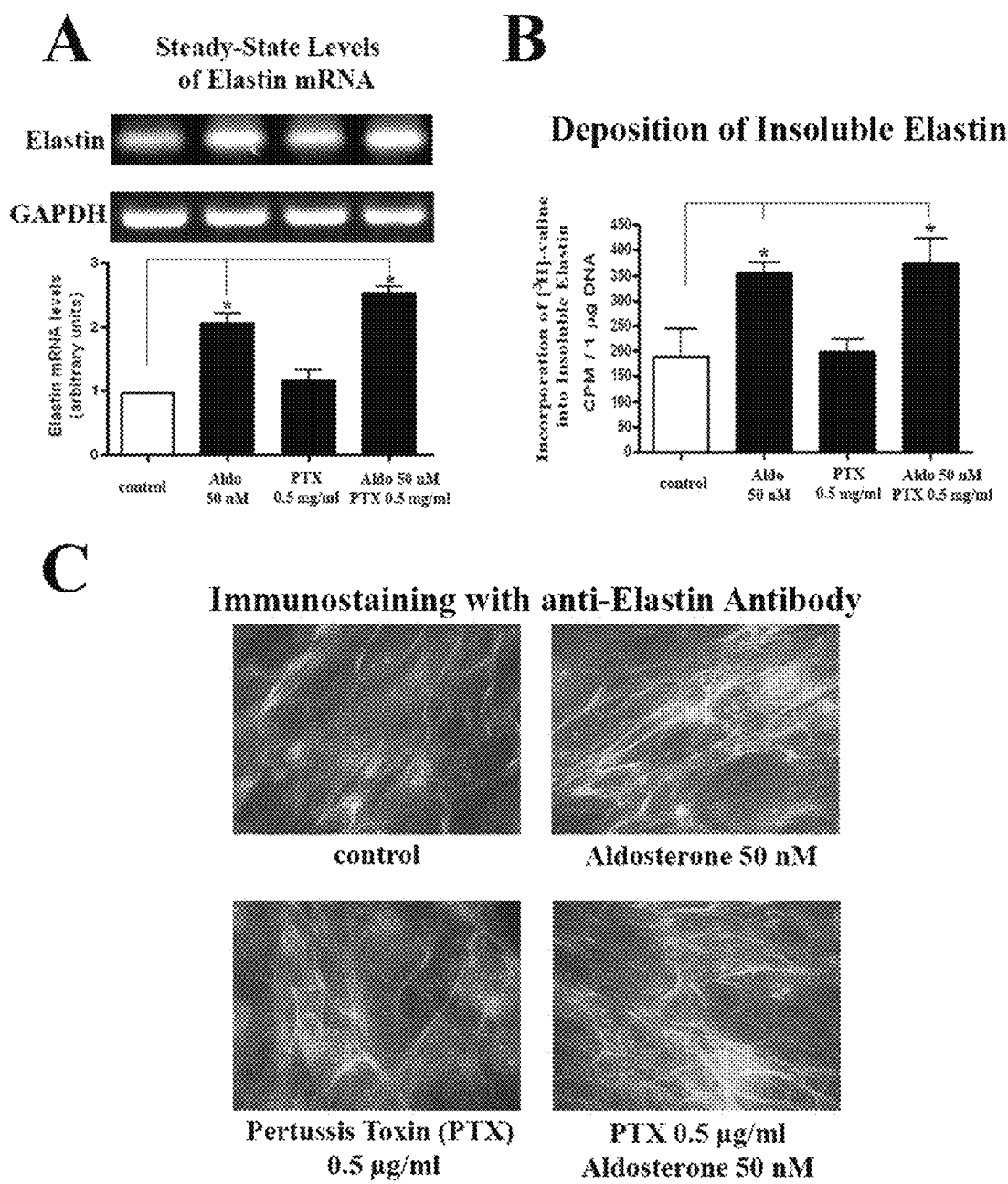
FIG. 8. The Gαi inhibitor pertussis toxin does not attenuate aldosterone-induced increases in elastin production in human cardiac fibroblast cultures. (A) Results of one-step RT-PCR analysis assessing elastin mRNA transcripts (normalized for GAPDH) in cultures treated for 24 hours with or without 50 nM of aldosterone prior to 1 hour pre-incubation with 0.5 mg/ml of pertussis toxin (PTX). (B) Results of a quantitative assay of [$^3$H]-valine-labeled insoluble elastin and (C) immunocytochemistry with anti-elastin antibody demonstrate that 1-hour pretreatment of cultures with 0.5 mg/ml of PTX following 72 hours incubation with 50 nM of aldosterone did not inhibit the elastogenic effect of aldosterone *(P<0.05). Initial magnification 600×.

Since other reports also suggested that certain MR-independent effects of aldosterone can be mediated by activation of the pertussis toxin-sensitive heterotrimeric G protein Gαi, we then tested its potential involvement in aldosterone-induced elastogenesis. However, the data we obtained demonstrated that pretreatment of cultured cardiac fibroblasts with pertussis toxin does not attenuate the pro-elastogenic effect of aldosterone (FIG. 8). Thus, the putative involvement of Gαi proteins in this process was also eliminated.

We therefore concentrated our investigation on another member of the G protein family, Gα13, which mediates nongenomic actions of estrogen.

Figure 9:
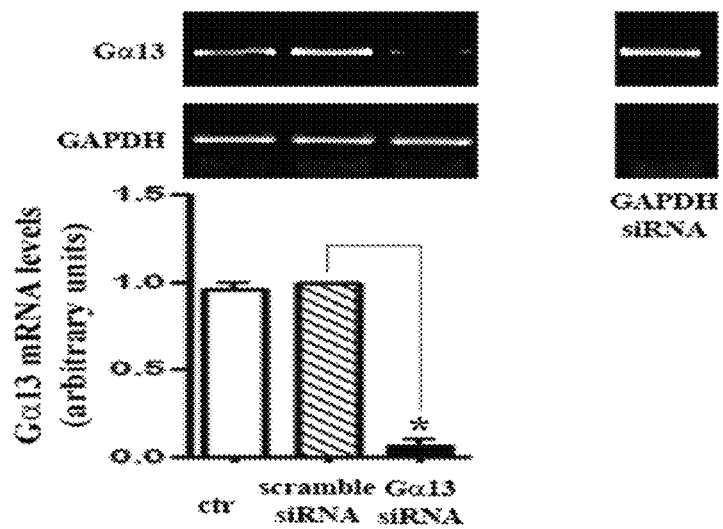
FIG. 9. Silencing Gα13 expression/production in human cardiac fibroblast cultures. (A) One-Step RT-PCR analysis assessing Gα13 and GAPDH mRNA transcript levels in a negative control culture, a scrambled siRNA control culture, and cultures containing Gα13 and GAPDH siRNA specific oligonucleotides, 24 hours after transfection. The results of densitometric evaluation demonstrate that Gα13 siRNA reduced Gα13 mRNA levels to approximately 8% of scrambled siRNA control levels 24 hours after transfection (*P<0.05). The graphs depict the mean±SD of data from three individual experiments in which Gα13 mRNA levels were normalized to the corresponding levels of GAPDH mRNA transcripts. GAPDH siRNA, which served as a positive control, completely eliminated GAPDH mRNA levels. (B) Representative Western blot of cellular lysates obtained from cultures that were transfected for either 48 hours or for 48 hours and then transfected again for an additional 72 hours (120 hours) with scrambled and Gα13 siRNA specific oligonucleotides, electrophoresed, and immunoblotted with anti-Gα13 antibody. The blots were then stripped and reprobed with anti-Gα12 and anti-α-actin antibodies. The graph depicts the densitometric evaluation of results obtained from three individual experiments. The mean±SD of data is expressed as a percentage of scrambled control Gα13 protein levels. Gα13 protein levels decreased to approximately 14% of the scrambled control levels 48 hours after transfection (P<0.05) and to approximately 9% of scrambled control levels 120 hours after transfection (*P<0.05).
Figure 9:
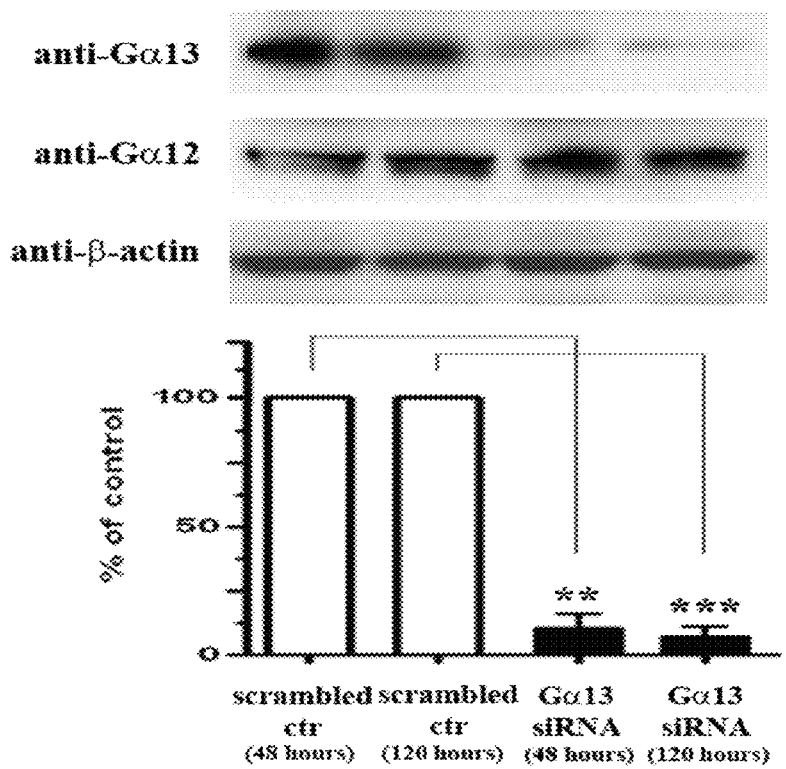
Figure 10A:
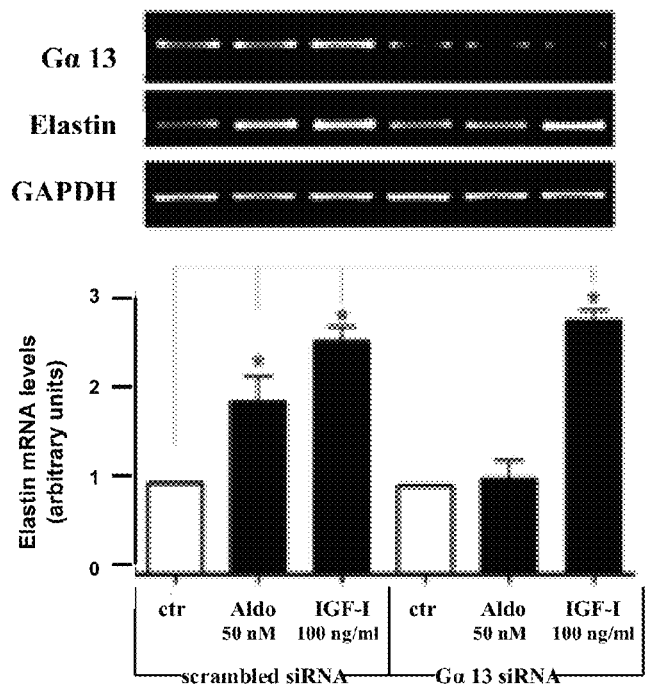
FIG. 10. Silencing Gα13 expression/production in cardiac fibroblast cultures attenuates the aldosterone-induced increase in elastin production and IGF-IR phosphorylation, but not the increase in collagen production. (A) Results of a one-step RT-PCR analysis assessing Gα13, elastin, and GAPDH mRNA transcript levels of cultures transfected for 72 hours with scrambled siRNA control and Gα13 siRNA specific oligonucleotides and treated for the last 24 hours with or without 50 nM of aldosterone or 100 ng/ml of IGF-I. The graphs depict the mean±SD of data from three individual experiments of elastin mRNA levels normalized to the corresponding levels of GAPDH mRNA transcripts. (B) Results of a quantitative assay of cultures of newly deposited insoluble elastin that were metabolically labeled with [$^3$H]-valine and initially transfected for 48 hours with scrambled or Gα13 siRNA and then transfected again for an additional 72 hours and kept in the presence or absence of 50 nM of aldosterone or 100 ng/ml of IGF-I. (C) Representative photomicrographs of confluent cultures immunostained with anti-elastin antibody confirm the results presented in (B). Initial magnification 600×. (D) Cultures were transfected for 72 hours with scrambled siRNA control and Gα13 siRNA specific oligonucleotides and treated for 10 minutes with or without 50 nM of aldosterone or 100 ng/ml of IGF-I. Cell lysates were immunoprecipitated (IP) with an IGF-IR antibody, electrophoresed, and probed with an anti-phospho-tyrosine (anti-phospho-tyr) antibody or anti-IGF-IR antibody. Graphs depict the mean±SD of data from three individual experiments, expressed as a percentage of control phosphorylation values obtained by normalizing to the corresponding total level of IGF-IR. (E) Results of a one-step RT-PCR analysis assessing collagen type I and GAPDH mRNA transcript levels of cultures transfected for 72 hours with scrambled siRNA control and Gα13 siRNA specific oligonucleotides and treated for the last 24 hours with or without 50 nM of aldosterone. The graphs depict the mean±SD of data from three individual experiments of collagen type I mRNA levels normalized to the corresponding levels of GAPDH mRNA transcripts. (F) Representative photomicrographs of confluent cultures immunostained with anti-collagen antibody that were initially transfected for 48 hours with scrambled or Gα13 siRNA and then transfected again for an additional 72 hours and kept in the presence or absence of 50 nM of aldosterone. *Statistically different from control group (P<0.05).
Figure 10B:
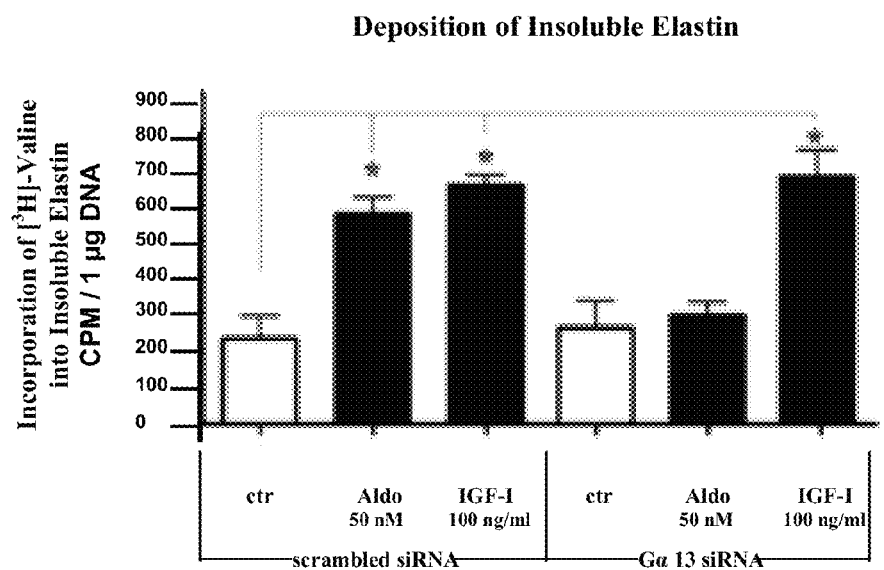
Figure 10C:
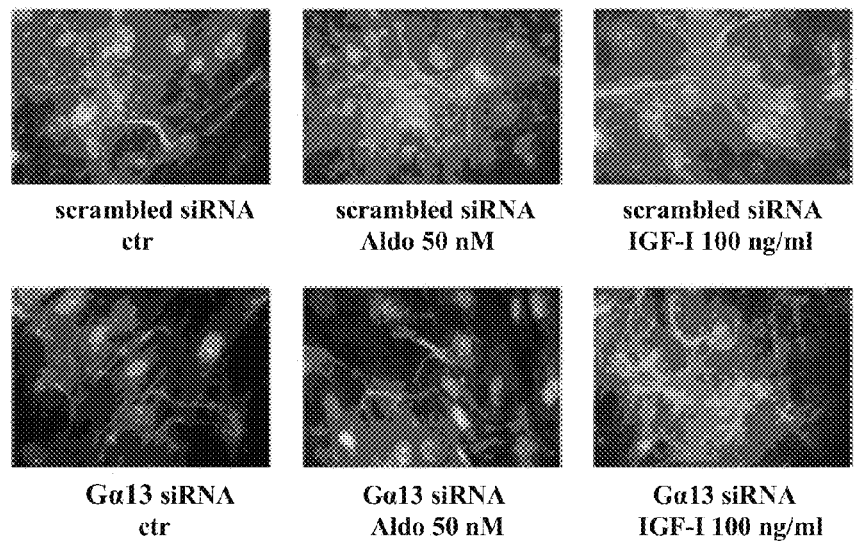
Figure 10D:
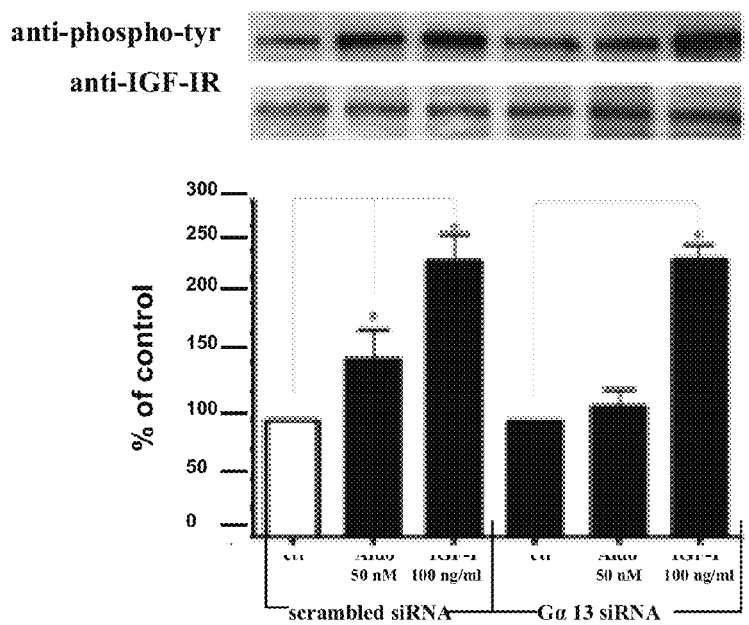
Figure 10E:
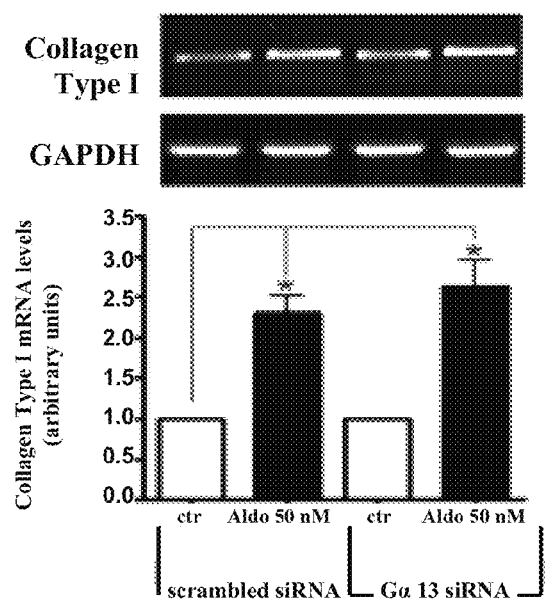
Figure 10F:
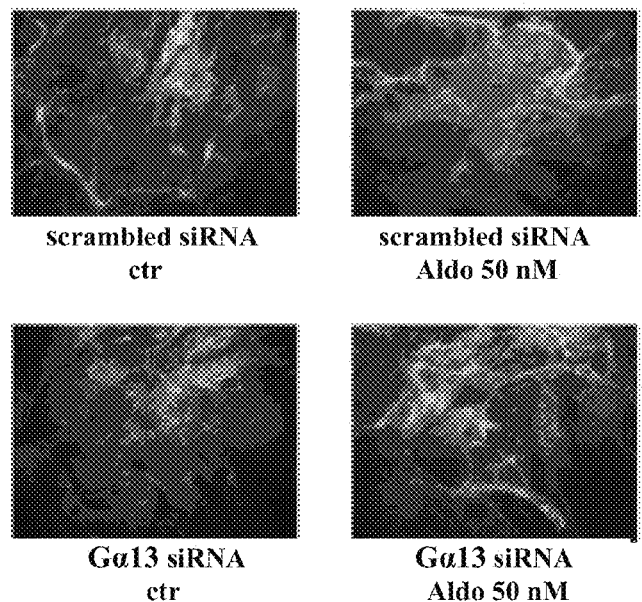

Silencing Gα13 in cardiac fibroblast cultures eliminates aldosterone-induced elastogenesis. In order to examine whether Gα13 would be involved in the initiation of the cellular signaling leading to an aldosterone-induced increase in elastin production, we specifically silenced Gα13 mRNA expression and protein production in cardiac fibroblast cultures without affecting the levels of its related family member, Gα12 (FIG. 9).

Figure 4A:
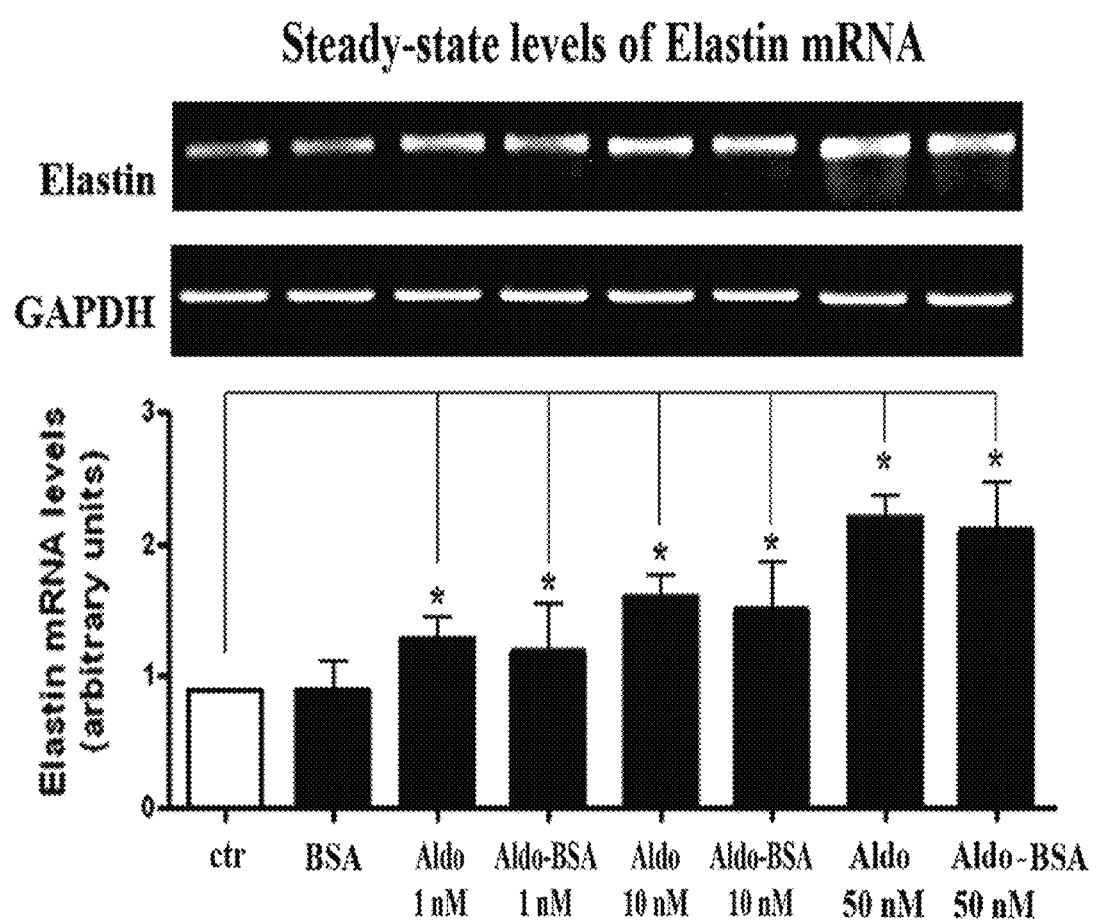
FIG. 4. The influence of cell-impermeable aldosterone conjugated to BSA on elastin mRNA levels and deposition of elastic fibers. Results demonstrate that 1 to 50 nmol/L aldosterone conjugated to BSA [aldo (1 to 50 nmol/L)-BSA] produced the same effect on elastin mRNA levels (A) and [$^3$H] valine incorporation (B) into insoluble elastin as 1 to 50 nmol/L aldosterone treatment alone. Cells treated with an equimolar concentration of BSA, as aldo (50 nmol/L)-BSA, served as an additional control. *Statistically different from control group (P<0.05).
Figure 4B:
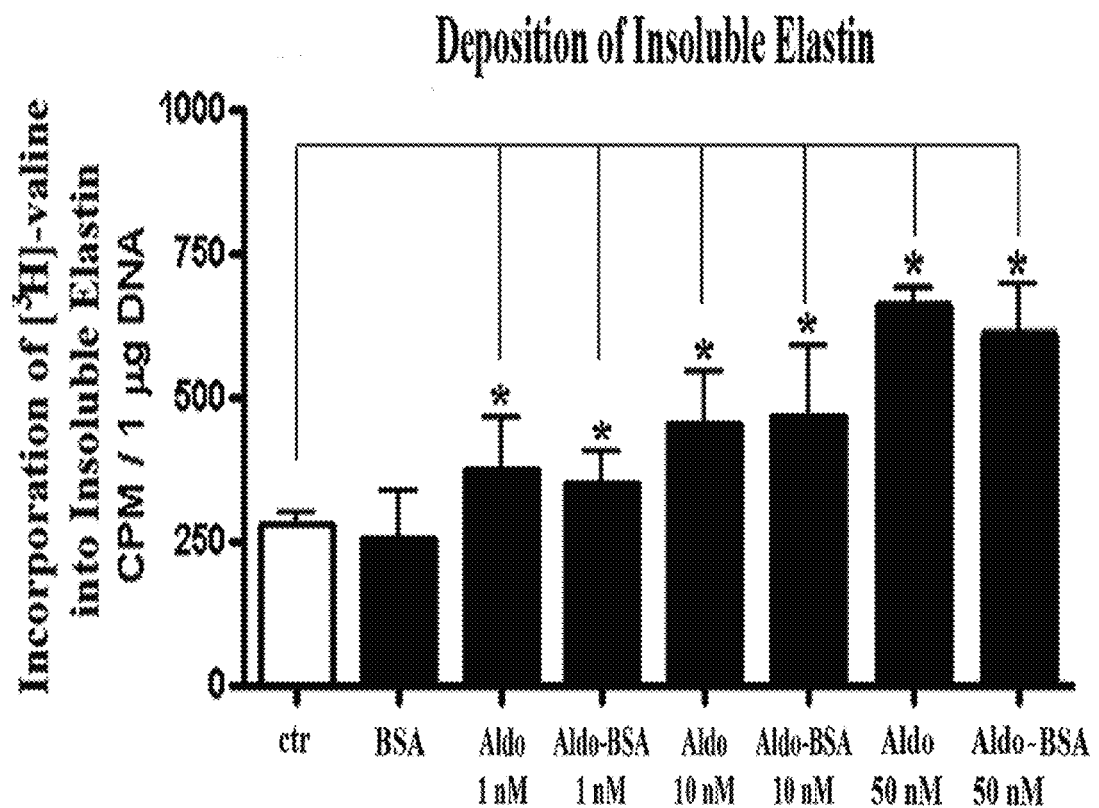
Figure 5A:
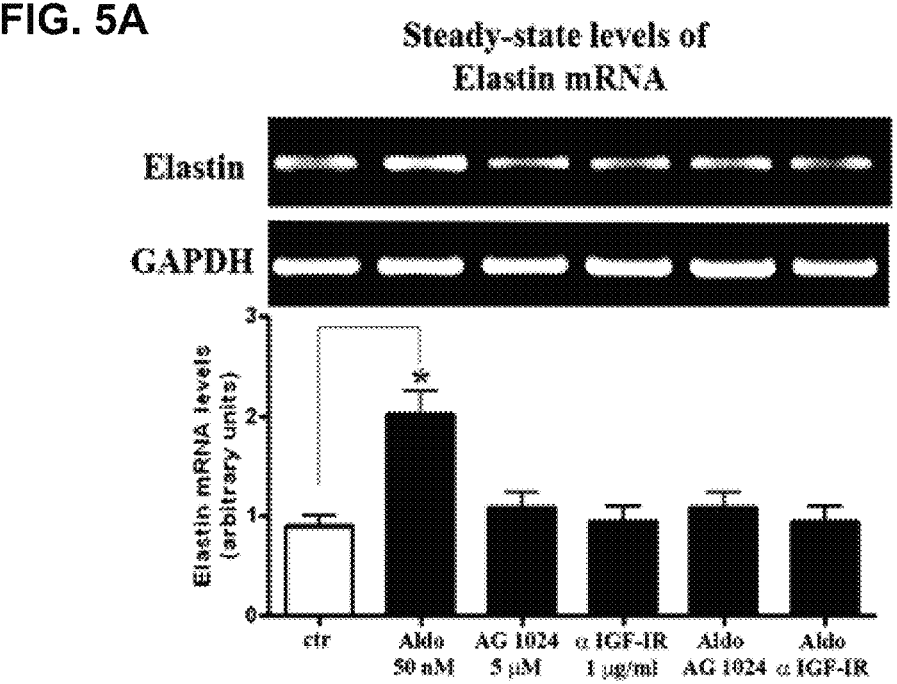
FIG. 5. IGF-IR inhibitor (AG 1024) and neutralizing antibody (er IGF-IR) antagonize aldosterone- and IGF-I-induced increases in elastin production in fetal cardiac fibroblast cultures. One-step RT-PCR analysis assessing elastin and GAPDH mRNA transcripts in cultures treated for 24 hours with 50 nmol/L aldosterone (A) or with 100 ng/ml IGF-I (B) before 1 hour of preincubation with 5 µmol/L AG 1024 or with 1 µg/ml αIGF-IR. The results show that inhibiting IGF-IR tyrosine kinase activity or blocking IGF-IR abolished aldosterone- and IGF-I-induced increases in elastin mRNA transcript levels. Incorporation of [$^3$H]valine (quantitative assay of insoluble elastin) demonstrated that cultures treated for 72 hours with 50 nmol/L aldosterone (C) or with 100 ng/ml IGF-I (D) before 1 hour of preincubation with 5 µmol/L AG 1024 or with 1 µg/ml βIGF-IR returned insoluble elastin production to control values. E: Representative photomicrographs of confluent cultures immunostained with anti-elastin antibody confirm the results presented in C. *Statistically different from control group (P<0.05).
Figure 5B:
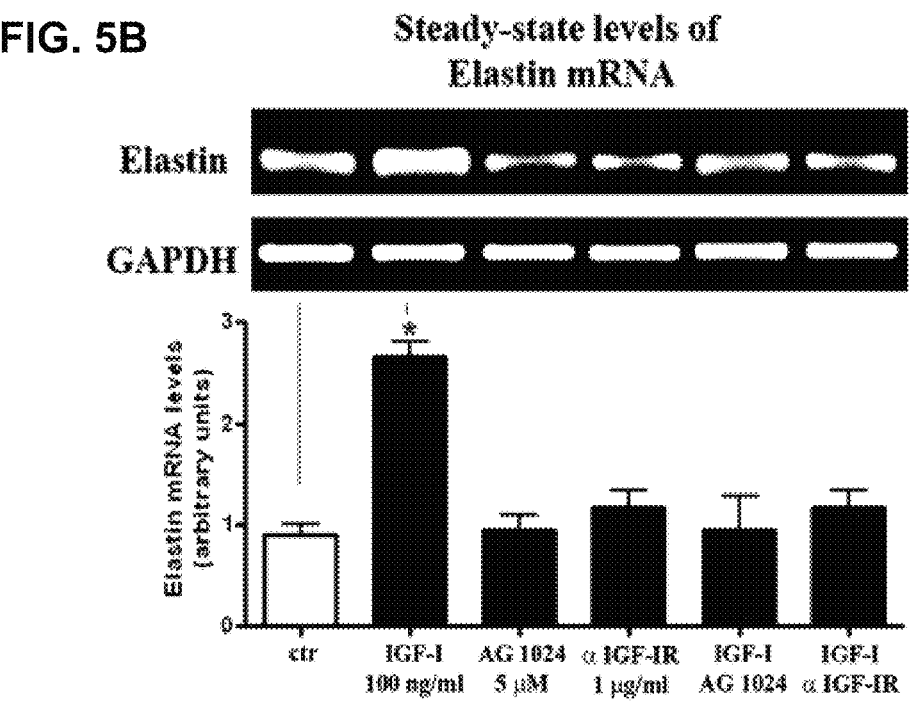
Figure 5C:
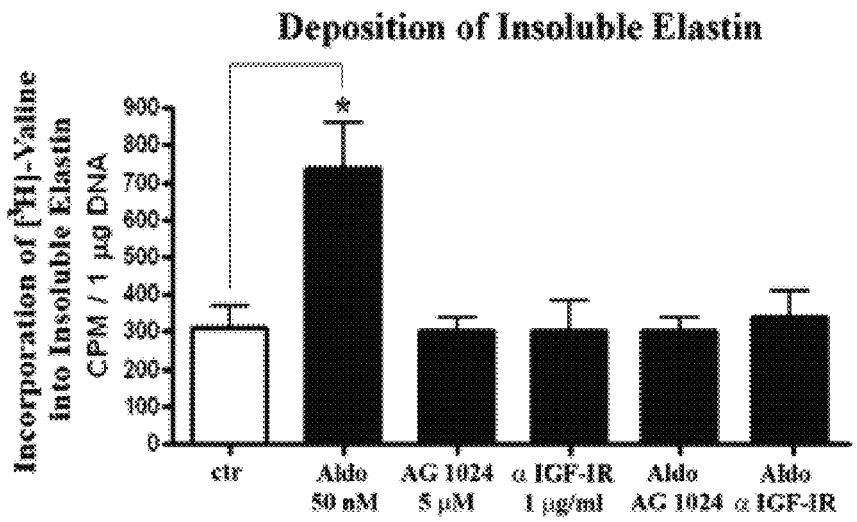
Figure 5D:
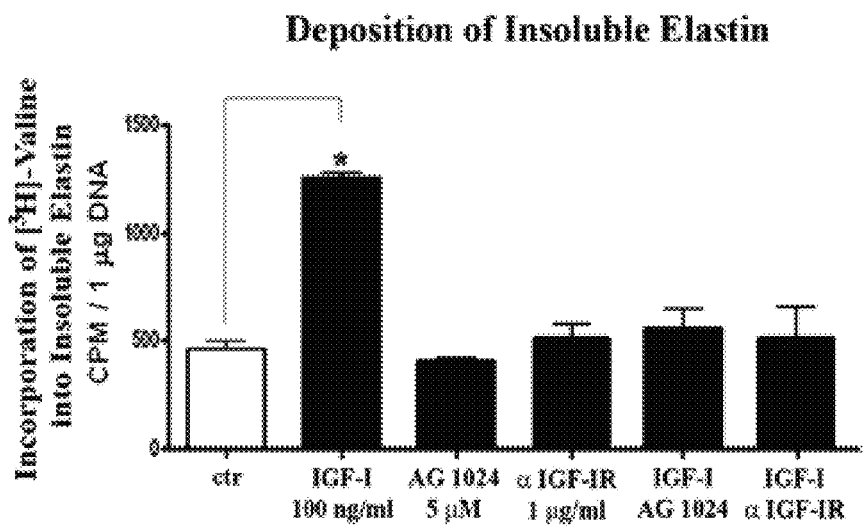
Figure 5E:
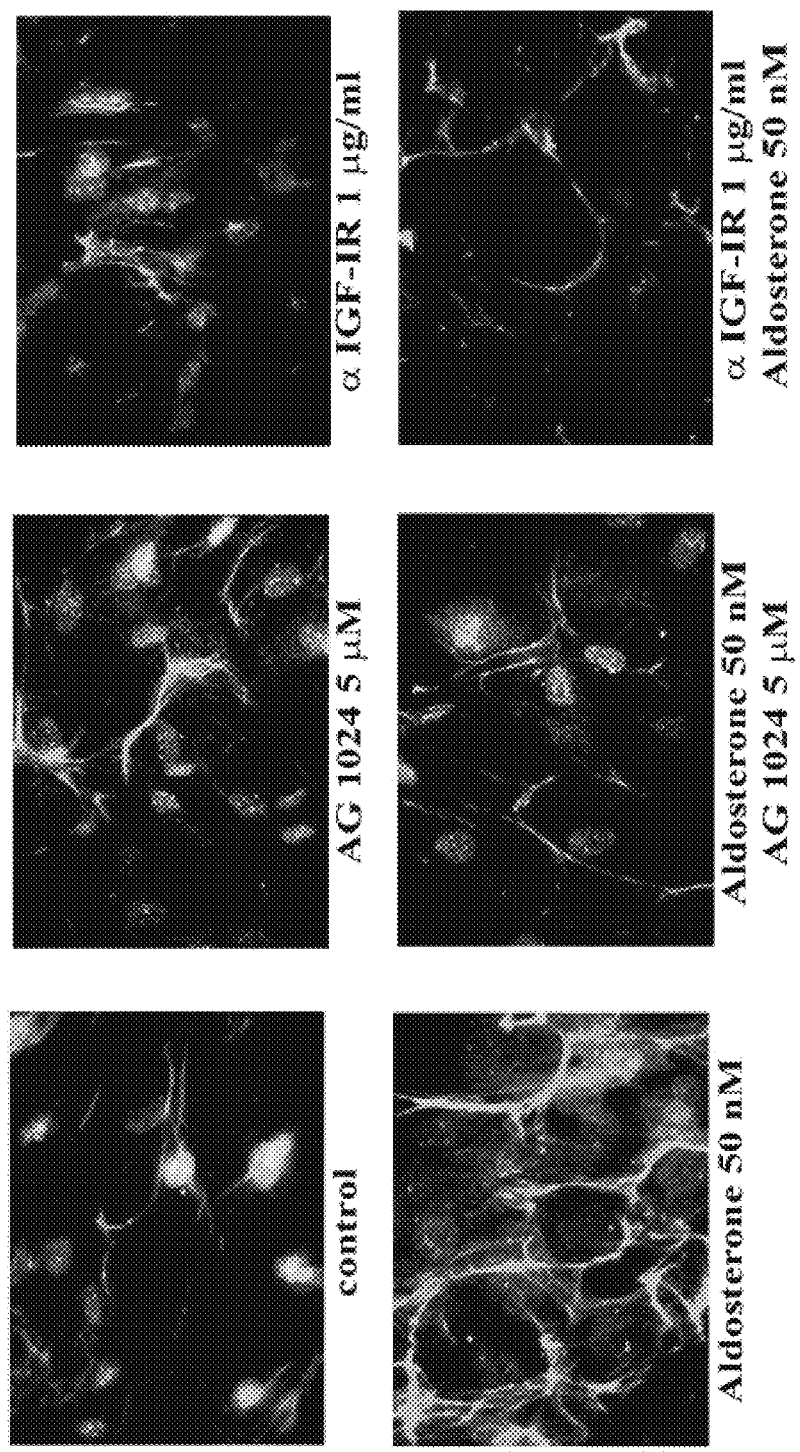

Our results indicated that the aldosterone-induced increase in elastin mRNA (observed in cultures transfected with scrambled siRNA) did not occur in cultures in which Gα13 expression was effectively silenced (FIG. 4A). Consequently, cultures of cardiac fibroblasts that were transfected with Gα13 siRNA did not demonstrate any increase in elastin deposition in response to aldosterone treatment (FIGS. 10 B and C). Meaningfully, parallel cultures transfected either with Gα13-specific or with scrambled siRNA demonstrated heightened elastin message levels and increased deposition of mature (metabolically labeled and immunodetectable) elastin in response to IGF-I treatment. Additionally, we found that in contrast to cultures transfected with scrambled siRNA, which demonstrated a significant increase in IGF-IR phosphorylation, cultures transfected with Gα13-specific siRNA did not demonstrate any upregulation in IGF-IR phosphorylation following aldosterone treatment (FIG. 10 D). We also demonstrated that Gα13 is not involved in the collagenogenic effect of aldosterone (FIGS. 10 E and F).

These results clearly demonstrated that Gα13 is engaged in the initial stage of the aldosterone-induced increase in elastogenesis that occurs prior to IGF-IR activation.

Figure 11A:
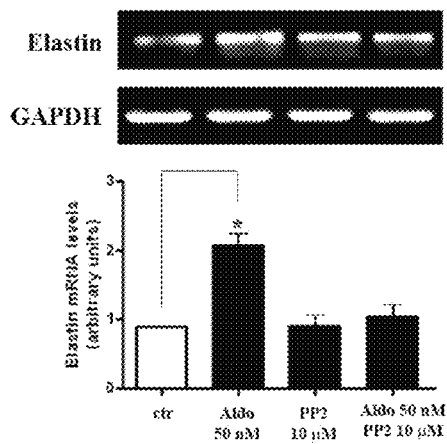
FIG. 11. c-Src tyrosine kinase inhibitor PP2 eliminates aldosterone-induced increases in elastin production in human cardiac fibroblast cultures. (A) Results of a one-step RT-PCR analysis assessing elastin and GAPDH mRNA transcripts in cultures maintained for 24 hours in the presence or absence of 50 nM aldosterone, with or without 1 hour pretreatment with 10 μM of PP2. (B) Results of [$^3$H]-valine-labeled insoluble elastin also demonstrate that PP2 treatment eliminated the aldosterone-induced increase in the net deposition of insoluble elastin. (C) Representative photomicrographs of confluent cultures immunostained with anti-elastin antibody confirm the results presented in (B). Initial magnification 600×. *Statistically different from control group (P<0.05).
Figure 11B:
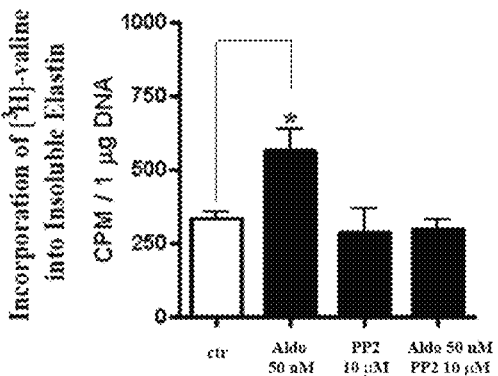
Figure 11C:
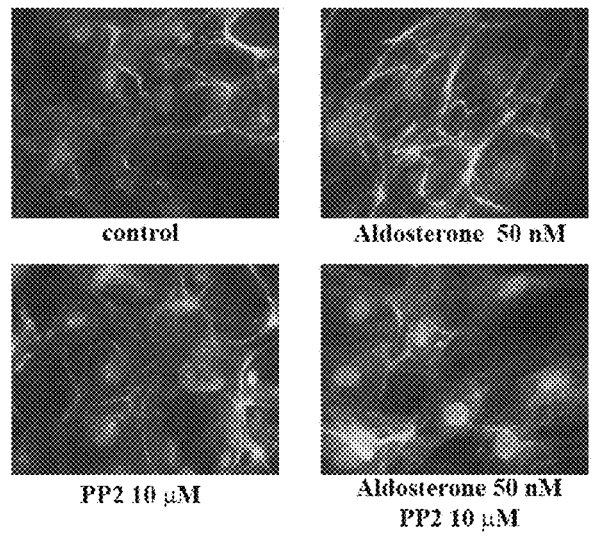
Figure 12A:
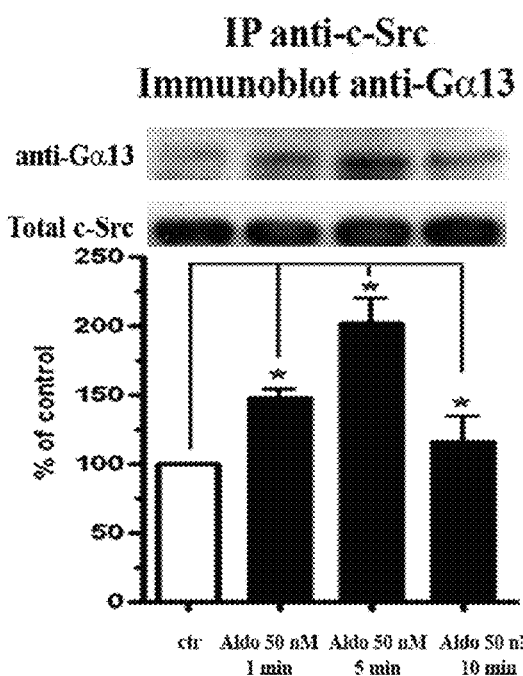
FIG. 12. Aldosterone treatment increases the interaction between Gα13 and c-Src, leading to activation of c-Src in human cardiac fibroblast cultures. (A) Cardiac fibroblast cultures were treated with or without 50 nM of aldosterone for 1, 5, and 10 minutes. Cell lysates were immunoprecipitated (IP) with anti c-Src antibody, electrophoresed, and probed with an anti-Gα13 antibody or anti-c-Src antibody. (B) Cellular lysates obtained from cultures treated with or without aluminum fluoride for 30 minutes were immunoprecipitated (IP) with anti-Gα13 antibody (left panel) or anti-c-Src antibody (right panel), electrophoresed, and Western blotted with an anti-c-Src antibody or anti-Gα13 antibody respectively. Total levels of Gα13 and c-Src were also assessed after stripping and reprobing the blots with their respective antibodies. Western blot analysis of cellular lysates obtained from cultures treated with or without 50 nM of aldosterone for 10 minutes (C) after they were preincubated for 1 hour in the presence or absence of 10 μM of PP2 or (D) following 72 hour transfection with scrambled siRNA control and Gα13 siRNA specific oligonucleotides, electrophoresed, and immunoblotted using anti-phospho-c-Src (Tyr416) and then stripped and reprobed with anti-c-Src antibody. Graphs depict the mean±SD of data from three individual experiments, expressed as a percentage of control values obtained by normalizing to the corresponding total level of c-Src or Gα13.
Figure 12B:
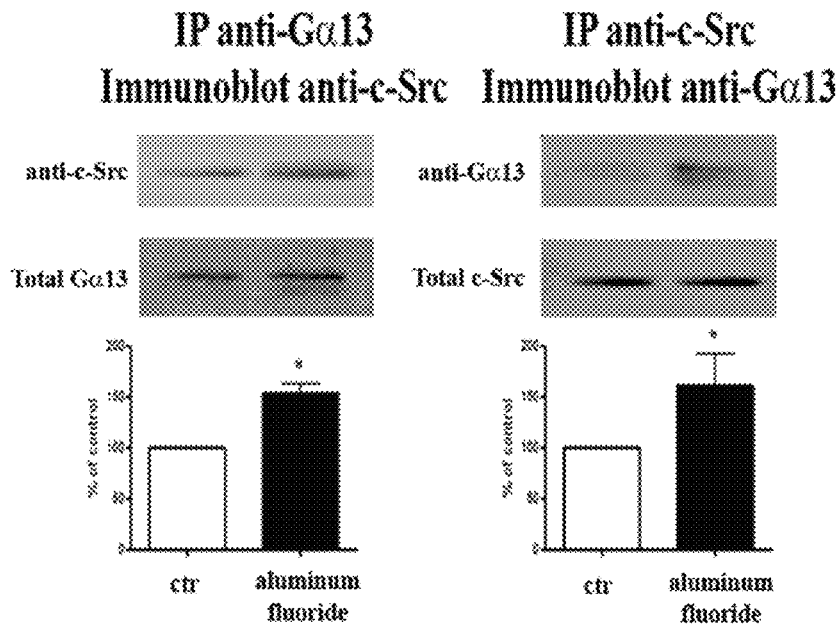
Figure 12C:
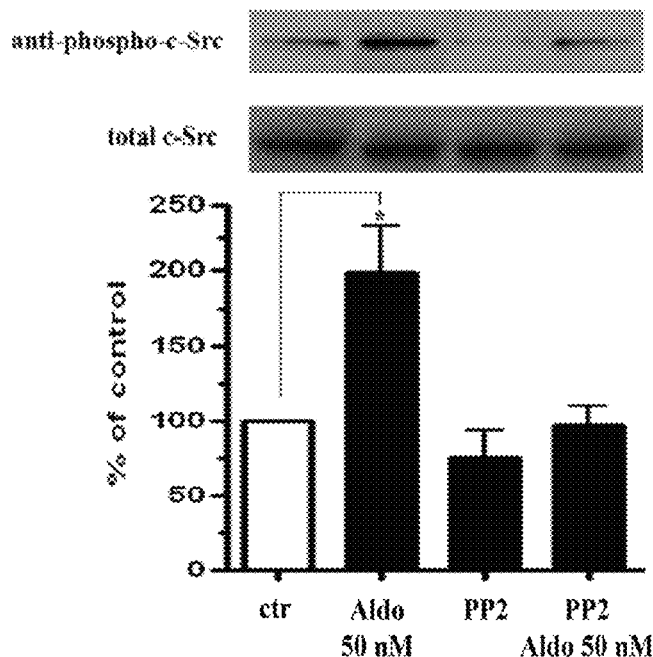
Figure 12D:
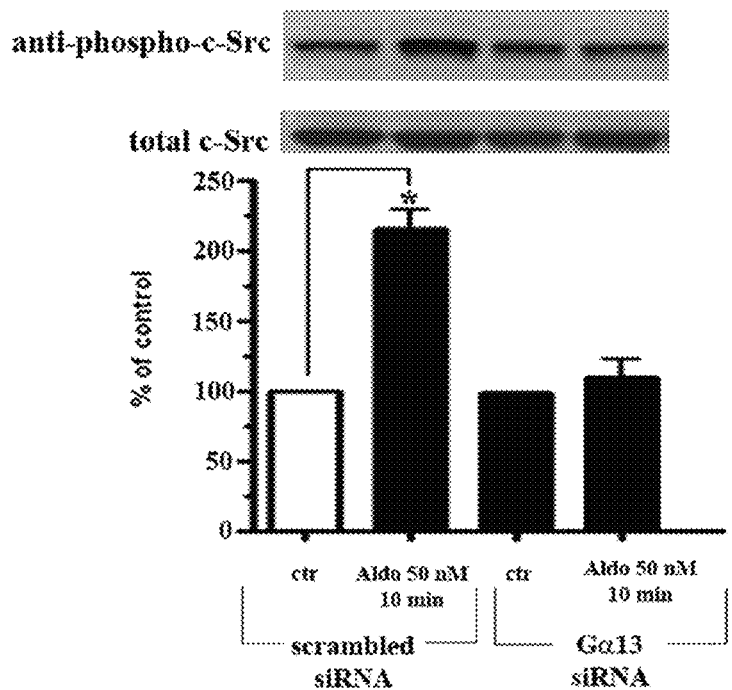
Figure 13A:
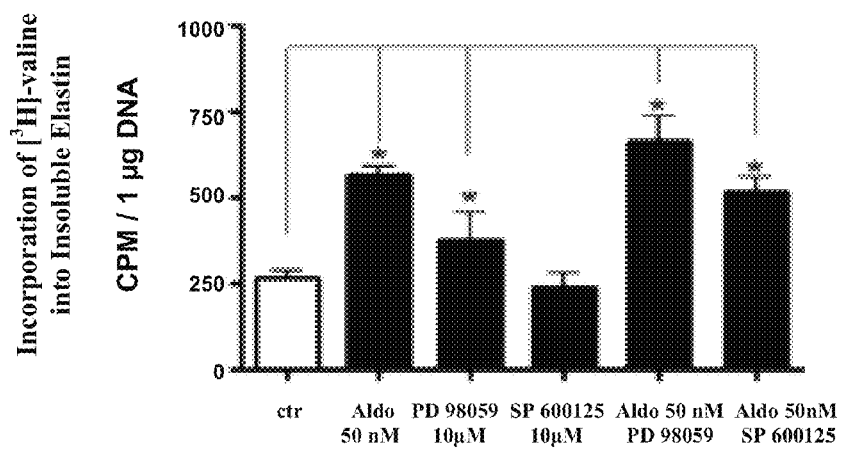
FIG. 13. The PI3 kinase/Akt signaling pathway propagates the aldosterone- or IGF-I-induced increases in elastin production in human cardiac fibroblast cultures. (A) Results of a quantitative assay of [$^3$H]-valine-labeled insoluble elastin demonstrate that cultures maintained in 10% FBS significantly increased insoluble elastin production when treated for 72 hours with 10 μM of PD 98059, compared to untreated control cultures (*P<0.05), and that the addition of 10 μM of PD 98059 prior to treatment with 50 nM of aldosterone further increased insoluble elastin production. In contrast, cultures treated with 10 μM of SP600125 prior to treatment with 50 nM of aldosterone showed no effect on the deposition of insoluble elastin. (B) Representative photomicrographs of confluent cultures immunostained with anti-elastin antibody confirm the results presented in (A). Initial magnification 600×. (C) Results of a one-step RT-PCR analysis assessing elastin and GAPDH mRNA transcripts in cultures maintained for 24 hours in the presence or absence of 50 nM aldosterone or 100 ng/ml of IGF-I, prior to 1 hour pretreatment with 1 μM of wortmannin. (D) Results of a quantitative assay of [$^3$H]-valine-labeled insoluble elastin demonstrate that treatment for 72 hours with 50 nM of aldosterone or with 100 ng/ml of IGF-I prior to 1 hour pretreatment with 104 of wortmannin returned insoluble elastin production to control values. Western blot analysis of cellular lysates obtained from cultures treated for 10 minutes with or without 50 nM of aldosterone after they were preincubated for 1 hour in the presence or absence of 10 μM of PP2 (E) or treated for 10 minutes with aldosterone or 100 ng/ml of IGF-I following 72 hour transfection with scrambled siRNA control and Gα13 siRNA specific oligonucleotides, electrophoresed, and immunoblotted using anti-phospho-Akt (Ser473) antibody and then stripped and reprobed with anti-Akt antibody. Graphs depict the mean±SD of data from three individual experiments, expressed as a percentage of control phosphorylation values obtained by normalizing to the corresponding total level of c-Src or Akt. The results of Western blot analysis demonstrate that exposure of cultures to aldosterone for 10 minutes leads to a significant increase in the basal phosphorylation of Akt and that either (E) PP2 pretreatment or (F) Gα13 siRNA transfection eliminates this effect. (G) One-step RT-PCR analysis assessing elastin and GAPDH mRNA transcripts in cultures treated for 30 minutes, 1, 3, 6, or 16 hours with or without 50 nM of aldosterone. *Statistically different from control group (P<0.05).
Figure 13B:
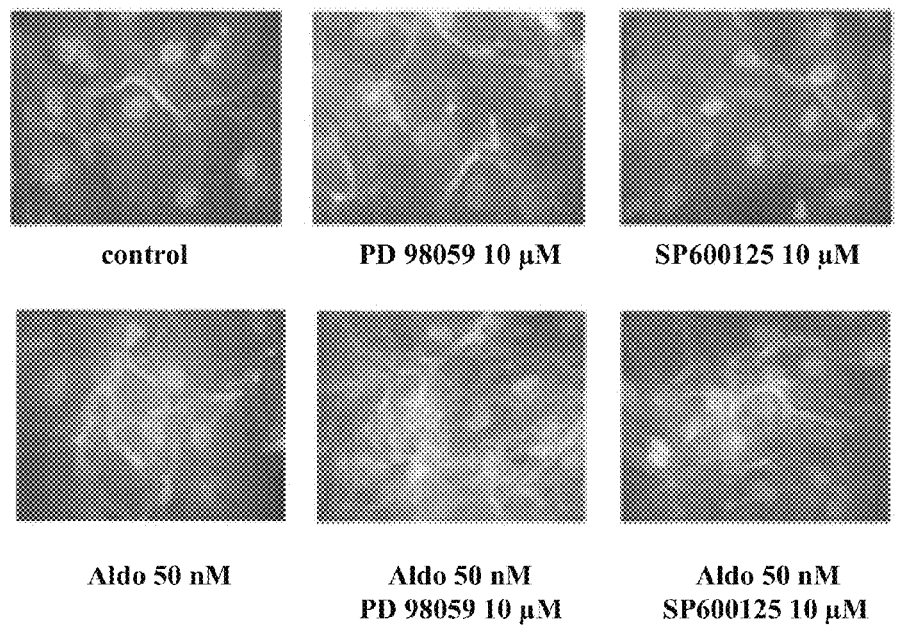
Figure 13C:
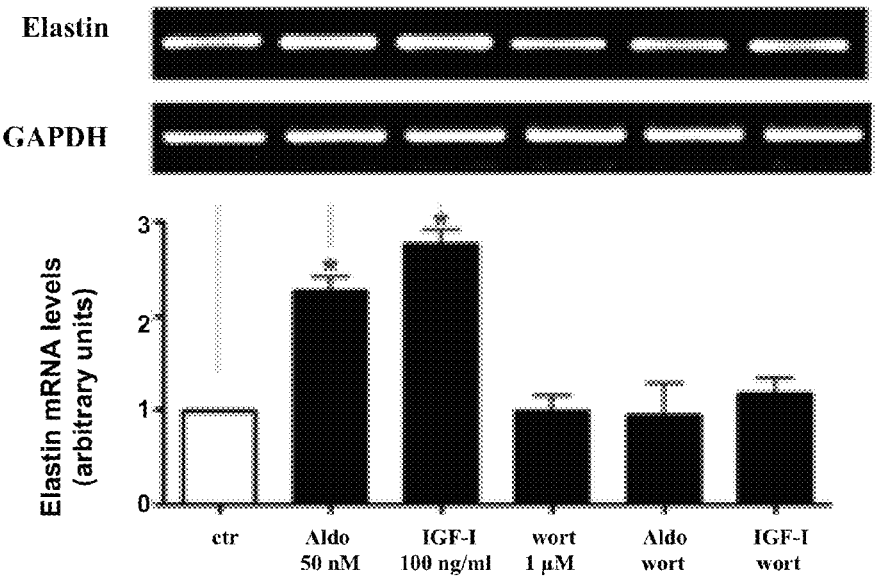
Figure 13D:
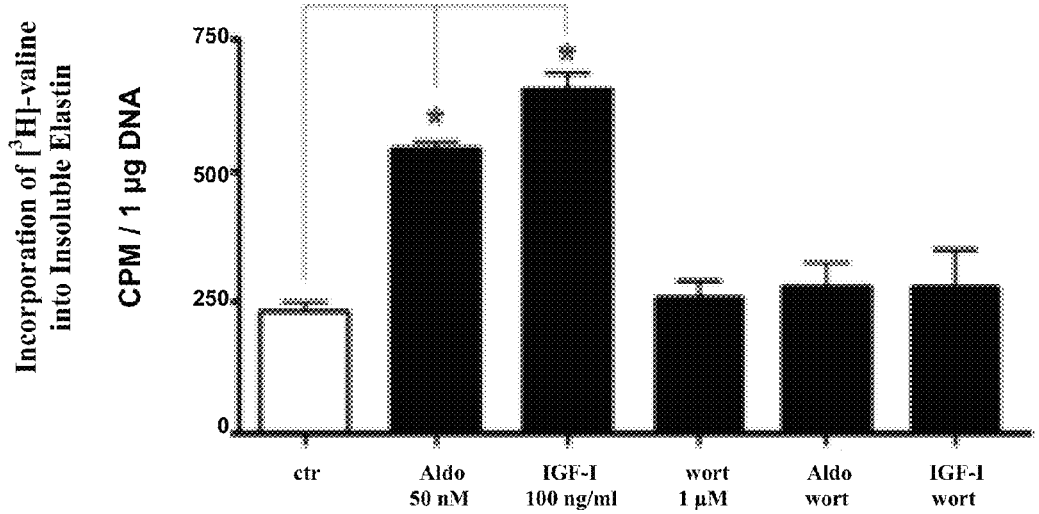
Figure 13E:
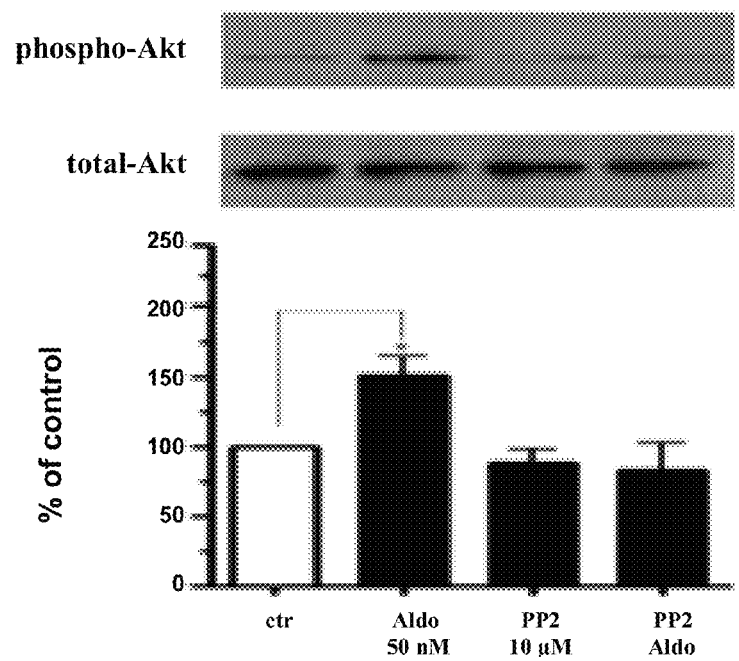
Figure 13F:
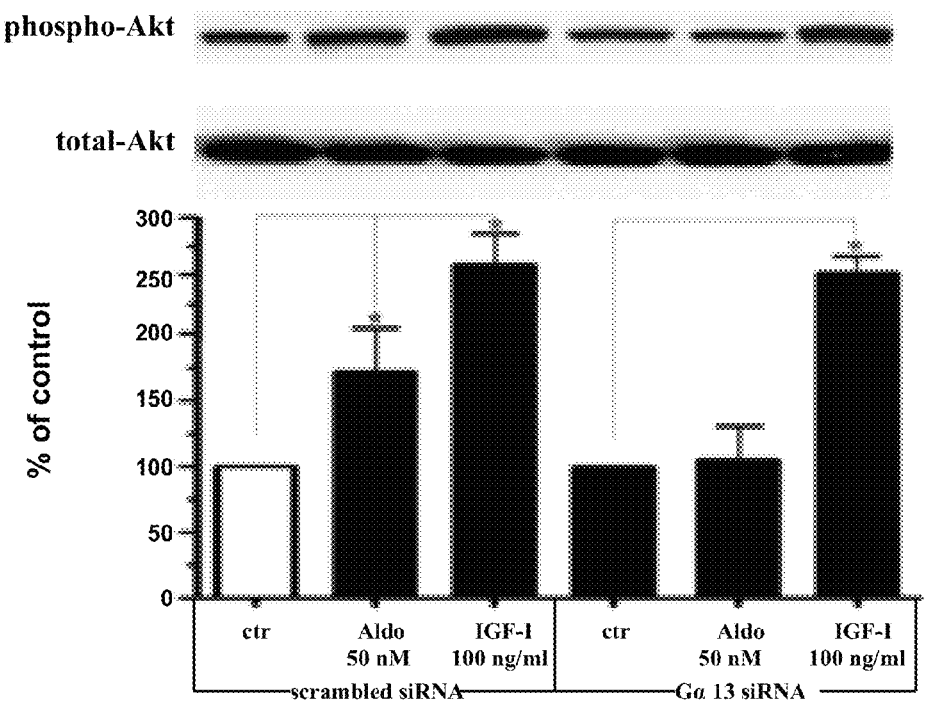
Figure 13G:
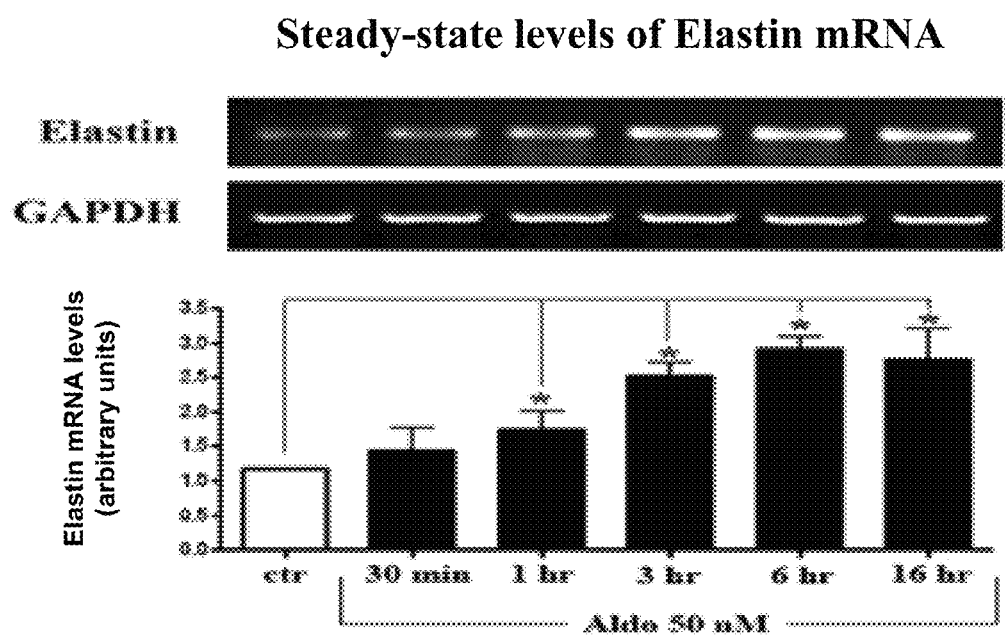
Figure 14:
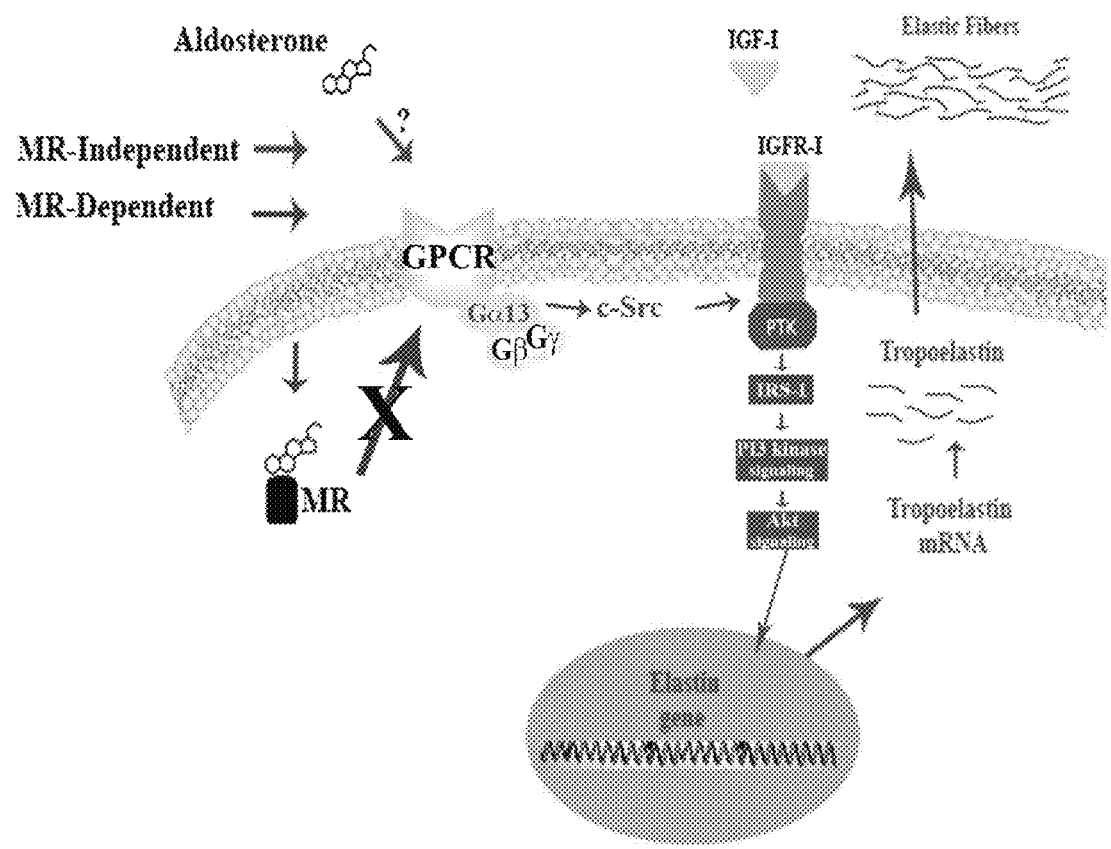
FIG. 14. Proposed mechanism by which aldosterone increases elastin production in cardiac fibroblast cultures. Aldosterone interacts with a GPCR that causes the activation of Gα13. Activated Gα13, in turn, interacts with cytosolic c-Src. This interaction facilitates the activation of IGF-IR-IRS/PI3 kinase/Akt signaling, which occurs even in the presence of sub-physiological levels of IGF-I, and subsequently induces increased elastin transcription and production. This effect of aldosterone is not dependent on the presence of the MR.

Aldosterone also induces a transient interaction between Gα13 and c-Src that leads to c-Src phosphorylation. Results from further experiments suggested that this initial Gα13-dependent effect may also involve the activation of cytosolic tyrosine kinase c-Src. This conclusion was based on the observation that pharmacological inhibition of c-Src (with PP2) abolished an increase in elastin mRNA levels and the consequent upregulation in elastic fiber production in aldosterone-treated cultures (FIG. 11).

Since the most characterized downstream signaling mediated by Gα13 involves GTPase Rho, we examined a possible involvement of Rho and its downstream effector, ROCK, in aldosterone-dependent elastogenesis. Because pretreatment of cultured cardiac fibroblasts, either with a cell membrane permeable Rho inhibitor, CT04, or with a specific ROCK inhibitor, Y-27632, did not eliminate the aldosterone-induced increase in elastin mRNA expression and elastin production in our cardiac fibroblast cultures, we concluded that the Rho pathway is not involved in the described elastogenic effect of aldosterone.

Instead, we have established that Gα13 transiently interacts with c-Src proteins following aldosterone treatment. This conclusion was based on results of experiments indicating that Gα13 and c-Src can be co-immunoprecipitated from cellular lysates that were maintained in the presence and absence of aldosterone for 1, 5, or 10 minutes. Interaction between these two proteins was most evident after 5 minutes of aldosterone exposure (FIG. 12 C).

We then investigated whether pharmacological activation of Gα13 enforces its transient association with c-Src. We found that a nonspecific activator of Ga proteins, aluminum fluoride, also increased the interaction between c-Src and Gα13 (FIG. 12 D left panel). Specifically, we found that c-Src immunoprecipitated from cellular lysates treated with aluminum fluoride consistently displayed greater interaction with Gα13 than untreated controls (FIG. 12 D right panel).

Since phosphorylation of c-Src at tyrosine 416 (Tyr416) in the activation loop of the kinase domain upregulates the enzymatic activity of c-Src, we then examined whether aldosterone treatment would increase c-Src phosphorylation at Tyr416. Indeed, Western blotting with a specific anti-phospho-c-Src (Tyr416) antibody indicated that lysates of cells treated with aldosterone displayed increased phosphorylation of c-Src on Tyr416, as compared to the control. We also demonstrated that PP2 pretreatment abolished this effect (FIG. 12 A). Importantly, we also found that the Gα13 siRNA-transfected cultures did not demonstrate any increase in c-Src phosphorylation in response to aldosterone treatment. This was in contrast to scrambled siRNA-transfected cultures, which demonstrated a significant increase in c-Src phosphorylation after treatment with aldosterone (FIG. 12 B). These results thus further enforced the notion that in cardiac fibroblasts aldosterone engages Gα13 signaling that in turn interacts with c-Src, causing its activation.

The PI3 Kinase/Akt signaling pathway propagates the elastogenic signal upon IGF-IR activation. Having established that the IGF-IR receptor mediates the effect of aldosterone on elastin production, we now attempted to determine which downstream IGF-IR signaling pathway, the PI3 kinase/Akt or the mitogen-activated protein kinases/extracellular signal-regulated kinases (MAPK/ERK) pathway, propagates the elastogenic signal. Results from metabolic labeling studies and immunofluorescence microscopy demonstrated that blocking the activation of the MAPK pathway by its specific MEK inhibitor, PD 98059, did not eliminate the elastogenic effect of aldosterone but instead led to a further increase in the production of elastin (FIGS. 13 A and B). Also, treatment with an inhibitor (SP600125) that inactivated another MAPK family member, JNK, did not diminish the elastogenic effect of aldosterone (FIGS. 13 A and B). On the other hand, results from one-step RT-PCR analysis and metabolic labeling studies demonstrated that the addition of the PI3 kinase inhibitor wortmannin to cultures treated with aldosterone or IGF-I abolished the elastogenic effects of both stimulators (FIGS. 13 C and D). These results indicate that the IGF-IR-PI3 kinase pathway propagates the elastogenic signal and that inhibition of the parallel MAPK pathway further enhances the net elastogenic effect.

In order to finally link the early steps of aldosterone-induced signaling (Gα13-dependent c-Src activation) with the downstream elastogenic pathway (PI3 kinase/Akt signaling transduced through the IGF-IR following its activation), we tested whether this IGF-IR-dependent downstream signaling event would still occur after inhibition of c-Src with PP2 and in cultures lacking Gα13. Western blot analysis using anti-phospho-Akt antibody revealed that the aldosterone-induced increase in the phosphorylation of Akt is indeed eliminated in cultures treated with the c-Src inhibitor PP2 and in cultures transfected with Gα13 siRNA (FIGS. 13 E and F). Furthermore we showed that the levels of tropoelastin mRNA begin to significantly increase as early as 1 hour after exposure to aldosterone, reach a maximum level between 3-6 hours, and remain elevated throughout the course of the experiment (FIG. 13 G). This endorsed the suggested link between the early aldosterone induced signaling and consequent increase in elastin mRNA steady-state levels.

Thus, the data presented reveal the details of an elastogenic signaling pathway that is triggered by aldosterone and involves the consecutive activation of Gα13, c-Src, and IGF-IR and its downstream PI3 kinase/Akt signaling.

Aldosterone stimulates elastogenesis via IGF-IR signaling in both fetal and adult and cultures of human cardiac fibroblasts, even in the presence of the MR-antagonist spironolactone. Results of the experiments presented in this report additionally demonstrate that aldosterone still induces elastogenesis in cardiac fibroblast cultures in which the synthesis of MR protein is inhibited by the use of MR-specific siRNA oligonucleotides. Thus, these data further confirm that the elastogenic effect of aldosterone is executed via an MR-independent mechanism. Moreover, we have established that membrane-impermeable, BSA-conjugated aldosterone produces the same magnitude of IGF-IR phosphorylation as equimolar concentrations of free aldosterone (FIG. 13). This suggests that the signaling pathway leading to the MR-independent elastogenic effect of aldosterone may be initiated after the interaction of this steroid hormone with a certain moiety residing on the cell surface of cardiac fibroblasts. This assumption is further supported by other studies that have demonstrated the existence of high affinity membrane binding sites for aldosterone in human vascular endothelium human mononuclear leukocytes and in pig kidneys and livers. It has also been suggested that a 50 kDa protein may meet the criteria for the alternative cell surface receptor for aldosterone.

G-protein-coupled receptors (GPCRs) are involved in the propagation of certain steroid receptor-independent effects of other steroid hormones in animals, and humans and that some MR-independent effects of aldosterone can also be mediated through pertussis toxin-sensitive Gαi proteins, therefore, we first investigated whether Gαi would propagate the elastogenic effect of aldosterone. However, the results of our experiments, as depicted in FIG. 8, excluded the possibility that activation of Gαi may be involved in aldosterone-induced elastogenesis. Instead, we demonstrated for the first time that another heterotrimeric Gα protein, a member of the G12 subfamily, Gα13, participates in a cellular response to aldosterone that involves IGF-IR activation and a consequent enhancement of elastogenesis. This conclusion was based on data indicating that the elimination of Gα13 in cultured cardiac fibroblasts by MR-specific siRNA oligonucleotides completely attenuated the aldosterone-induced increase in IGF-IR phosphorylation and subsequent elastin production (FIGS. 9 and 10). At the same time we also demonstrated that the absence of the Gα13 protein did not eliminate the elastogenic response of IGF-I (FIG. 10). This also reinforced our belief that Gα13 is located upstream of the IGF-IR in the elastogenic signaling pathway triggered by aldosterone.

Gα13 also stimulates the activation of the cytosolic tyrosine kinase c-Src in various cell types, including cardiac fibroblast cultures. The results of our co-immunoprecipitation experiments demonstrated that treatment with aldosterone enhances the transient interaction between Gα13 and c-Src (FIG. 12). Since the inactivation of c-Src (by its specific PP2 inhibitor) eliminated the elastogenic effect of aldosterone, we concluded that the action of this kinase constitutes a prerequisite for the propagation of the aldosterone-dependent elastogenic signal (FIGS. 11 and 12).

Gα13 can directly bind and activate various proteins, including cytosolic tyrosine kinases such as Pyk2. The aldosterone-triggered interaction between Gα13 and c-Src is either direct, or it requires other proteins, such as Pyk2, that might bind and facilitate phosphorylation of c-Src. We have established that in aldosterone-treated cardiac fibroblasts, Gα13 stimulates phosphorylation of c-Src, via the Rho-independent pathway, and that the consecutive steps of elastogenic signaling involve increased phosphorylation of the IGF-IR and its downstream PI3 kinase/Akt signaling pathway (FIG. 7).

c-Src may not only phosphorylate the IGF-IR on ligand-induced auto-phosphorylation sites but also significantly increase the phosphorylation of this receptor on Tyr-1316, which has been implicated as a potential PI3 kinase binding site. Therefore, aldosterone-induced Gα13/c-Src activation facilitates IGF-IR signaling by enhancing its Tyr-1316 phosphorylation. This in turn selectively promotes the downstream PI3 kinase/Akt pathway needed for elastogenesis, but not the alternative IGF-IR-propagated mitogenic MAPK/ERK signaling pathway. Our data indicate that the aldosterone-induced elastogenic effect was enhanced in the presence of the MEK inhibitor PD 98059. Also, treatment with an inhibitor (SP600125) inactivating JNK, another MAPK family member, did not diminish the elastogenic effect of aldosterone (FIGS. 7 A and B).

Since phosphorylation on Tyr-1316 of the insulin receptor, which is closely related to the IGF-IR, has been shown to play an inhibitory role in mitogenic signaling, aldosterone-induced signaling enhancing phosphorylation of Tyr-1316 on the IGF-IR contribute to the mechanism maintaining the balance between signals stimulating differentiation and mitogenesis.

In aortic smooth muscle cells, IGF-I induces an increase in elastin gene expression via a derepressive mechanism involving the abrogation of Sp3, a retinoblastoma protein (Rb) associated element, that allows for activation of the elastin promoter by Rb on its retinoblastoma control element. Since Rb lies downstream of the PI3 kinase/Akt/mammalian target of rapamycin (mTOR) signaling pathway, aldosterone-dependent activation of this signaling pathway also modulates the interaction between Rb and pro-elastogenic transcription factors, leading to an increase in elastin gene expression in cardiac fibroblasts. Since we found that inhibition of the promitogenic MAPK/ERK signaling pathway further enhanced the effect of aldosterone on elastin production (FIGS. 7 A and B), we also suggest that the PI3 kinase/Akt signaling pathway induces elastogenesis by altering the phosphorylation state of Rb, while the mitogenic MAPK/ERK pathway antagonizes this effect. Interestingly, a similar pro-elastogenic effect involving the PI3 kinase/Akt signaling pathway exsits in lung fibroblasts after exposure to TGF-β.

In summary, data presented in this study suggest that the elastogenic effect of aldosterone in cardiac fibroblasts is propagated through the MR-independent action of this hormone. This novel mechanism likely involves a GPCR (or GPCRs) that couples to Gα13 to stimulate c-Src, which in turn facilitates the activation of tyrosine kinase-dependent phosphorylation of the IGF-IR and its downstream PI3 kinase signaling pathway (FIG. 8). This signaling pathway ultimately leads to the upregulation of the elastin gene and the efficient production of elastic fibers by cardiac fibroblasts. The heightened production of elastic fibers that results from the MR-independent action of aldosterone counterbalances MR-mediated maladaptive fibrosis in the post-infarct heart in patients using MR antagonists, thus providing resilience to the cardiac stroma and facilitating normal ventricular function.

Although the present invention has been described in considerable detail with reference to certain preferred embodiments thereof, other versions are possible. Therefore, the spirit and scope of the appended claims should not be limited to the description and the preferred embodiments disclosed herein.

The invention claimed is:

1. A method of treating cardiac dysfunction in a subject with a post-infarct heart comprising:
    administering an effective amount of aldosterone and an effective amount of spironolactone to said subject.

2. The method of claim 1, wherein the aldosterone and the spironolactone are administered by a method selected from the group consisting of local administration and systemic administration.

3. The method of claim 1, wherein the aldosterone and the spironolactone are administered by a mode selected from the group consisting of topical, parenteral, plural infusion, pericardial infusion, subcutaneous, intravenous, intraperitoneal, transdermal, oral, buccal, inhalation, depot injection, and implantation.

4. The method of claim 1, wherein the aldosterone and the spironolactone affect the cardiac fibroblasts in a mineralocorticoid receptor independent manner.

5. The method of claim 1, wherein the aldosterone and the spironolactone are administered simultaneously.

6. The method of claim 1, wherein the spironolactone is administered prior to the aldosterone.

7. A method of improving the ejection fraction in a post-infarct heart of a subject comprising:
    administering an effective amount of aldosterone and an effective amount of spironolactone to said subject.

8. The method of claim 7, wherein the aldosterone and the spironolactone are administered by a method selected from the group consisting of local administration and systemic administration.

9. The method of claim 7, wherein the aldosterone and the spironolactone are administered by a mode selected from the group consisting of topical, parenteral, plural infusion, pericardial infusion, subcutaneous, intravenous, intraperitoneal, transdermal, oral, buccal, inhalation, depot injection, and implantation.

10. The method of claim 7, wherein the aldosterone and the spironolactone affect the cardiac fibroblasts in a mineralocorticoid receptor independent manner.

11. The method of claim 7, wherein the aldosterone and the spironolactone are administered simultaneously.

12. The method of claim 7, wherein the spironolactone is administered prior to the aldosterone.

* * * * *

```
                        SEQUENCE LISTING

<160> NUMBER OF SEQ ID NOS: 4

<210> SEQ ID NO 1
<211> LENGTH: 6
<212> TYPE: PRT
<213> ORGANISM: Artificial sequence
<220> FEATURE:
<223> OTHER INFORMATION: Synthetic peptide

<400> SEQUENCE: 1

Val Gly Ala Met Pro Gly
1               5

<210> SEQ ID NO 2
<211> LENGTH: 6
<212> TYPE: PRT
<213> ORGANISM: Artificial sequence
<220> FEATURE:
<223> OTHER INFORMATION: Synthetic peptide

<400> SEQUENCE: 2

Val Gly Leu Ser Pro Gly
1               5

<210> SEQ ID NO 3
<211> LENGTH: 6
<212> TYPE: PRT
<213> ORGANISM: Artificial sequence
<220> FEATURE:
<223> OTHER INFORMATION: Synthetic peptide

<400> SEQUENCE: 3

Ile Gly Ala Met Pro Gly
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Ile Gly Leu Ser Pro Gly
1               5
```